US010369101B2

(12) United States Patent
Okumu et al.

(10) Patent No.: US 10,369,101 B2
(45) Date of Patent: Aug. 6, 2019

(54) PARENTERAL DICLOFENAC COMPOSITION

(71) Applicant: LATITUDE PHARMACEUTICALS INC., San Diego, CA (US)

(72) Inventors: Franklin Okumu, Morristown, NJ (US); Andrew X. Chen, San Diego, CA (US); Hailiang Chen, San Diego, CA (US)

(73) Assignee: LATITUDE PHARMACEUTICALS INC., San Diego, CA (US)

( * ) Notice: Subject to any disclaimer, the term of this patent is extended or adjusted under 35 U.S.C. 154(b) by 0 days.

(21) Appl. No.: 14/777,193

(22) PCT Filed: Mar. 17, 2014

(86) PCT No.: PCT/US2014/030519
§ 371 (c)(1),
(2) Date: Sep. 15, 2015

(87) PCT Pub. No.: WO2014/145710
PCT Pub. Date: Sep. 18, 2014

(65) Prior Publication Data
US 2016/0038414 A1 Feb. 11, 2016

Related U.S. Application Data

(60) Provisional application No. 61/793,356, filed on Mar. 15, 2013.

(51) Int. Cl.
*A61K 9/107* (2006.01)
*A61K 31/196* (2006.01)
(Continued)

(52) U.S. Cl.
CPC .......... *A61K 9/1075* (2013.01); *A61K 9/0019* (2013.01); *A61K 31/196* (2013.01);
(Continued)

(58) Field of Classification Search
CPC .... A61K 31/196; A61K 45/06; A61K 9/0019; A61K 9/1075; A61K 47/26; A61K 47/44; A61K 47/24
See application file for complete search history.

(56) References Cited

U.S. PATENT DOCUMENTS 3,558,690 A 1/1971 Metz
4,309,421 A 1/1982 Ghyczy et al.
(Continued)

FOREIGN PATENT DOCUMENTS

AT 410895 B 8/2003
CN 101244278 A 8/2008
(Continued)

OTHER PUBLICATIONS

Dyloject, FDA approved 19888; http://www.accessdata.fda.gov/drugsatfda_docs/label/2014/022396lbl.pdf.*
(Continued)

*Primary Examiner* — Blessing M Fubara
(74) *Attorney, Agent, or Firm* — Kilpatrick Townsend & Stockton LLP

(57) ABSTRACT

The present application provides parenteral compositions of diclofenac or its pharmaceutically acceptable salt and methods for making and using such compositions. Some of the compositions of the present application has one or more following properties: (1) ready to be injectable, (2) in the form of an oil-in-water emulsion, (3) stable under appropriate storage conditions, (4) containing therapeutically effective amount of diclofenac or its pharmaceutically acceptable salt, (5) sterilizable by filtration (6) containing components acceptable by regulatory agencies (e.g. the FDA), (7) containing low oil content and thus not exacerbating hyerlipidemia, and (8) is neither hyperallergenic nor vein irritating.

13 Claims, 4 Drawing Sheets

Phase diagram depicting a "nanoemulsion region" (grey area), which is defined by connecting lines between five compositions (A, B, C, D and E).

(51) Int. Cl.
*A61K 9/00* (2006.01)
*A61K 45/06* (2006.01)
*A61K 47/26* (2006.01)
*A61K 47/44* (2017.01)
*A61K 47/24* (2006.01)

(52) U.S. Cl.
CPC .............. *A61K 45/06* (2013.01); *A61K 47/24* (2013.01); *A61K 47/26* (2013.01); *A61K 47/44* (2013.01)

(56) References Cited

U.S. PATENT DOCUMENTS

| | | | |
|---|---|---|---|
| 4,593,044 | A | 6/1986 | Metz |
| 4,711,906 | A | 12/1987 | von Stetten et al. |
| 5,098,606 | A | 3/1992 | Nakajima et al. |
| 5,171,737 | A | 12/1992 | Weiner et al. |
| 5,283,067 | A | 2/1994 | Geller et al. |
| 5,338,761 | A | 8/1994 | Nakajima et al. |
| 5,356,633 | A | 10/1994 | Woodle et al. |
| 5,389,681 | A | 2/1995 | Galli |
| 5,554,650 | A | 9/1996 | Holl et al. |
| 5,626,873 | A | 5/1997 | Weiner et al. |
| 5,679,660 | A | 10/1997 | Bodley et al. |
| 5,693,337 | A | 12/1997 | Suzuki et al. |
| 6,007,826 | A * | 12/1999 | Benita ................ A61K 8/06 424/401 |
| 6,383,471 | B1 | 5/2002 | Chen et al. |
| 7,115,586 | B2 | 10/2006 | Loftsson |
| 7,422,028 | B2 | 9/2008 | Nugent et al. |
| 7,423,028 | B2 | 9/2008 | Zoppetti et al. |
| 7,871,632 | B2 | 1/2011 | Chen |
| 8,026,250 | B2 | 9/2011 | Chen |
| 8,222,268 | B2 | 7/2012 | Chen |
| 8,470,873 | B2 | 6/2013 | Chen |
| 8,557,861 | B2 | 10/2013 | Chen |
| 2002/0107265 | A1* | 8/2002 | Chen ................... A61K 9/1075 514/310 |
| 2003/0191187 | A1 | 10/2003 | Lee et al. |
| 2005/0058699 | A1 | 3/2005 | Lichtenberger et al. |
| 2006/0100288 | A1* | 5/2006 | Bague ................. A61K 9/0048 514/642 |
| 2007/0232566 | A1 | 10/2007 | Wright et al. |
| 2007/0232567 | A1 | 10/2007 | Wright et al. |
| 2008/0051373 | A1 | 2/2008 | Lichtenberger et al. |
| 2008/0153914 | A1* | 6/2008 | Patel ................... A61K 9/0019 514/567 |
| 2011/0065677 | A1 | 3/2011 | Lichtenberger |
| 2011/0200657 | A1 | 8/2011 | Baker |
| 2011/0218247 | A1 | 9/2011 | Wright et al. |
| 2012/0142779 | A1 | 6/2012 | Penkler et al. |
| 2012/0328675 | A1* | 12/2012 | Awamura ............. A61K 31/045 424/400 |
| 2013/0079334 | A1 | 3/2013 | Chen et al. |
| 2013/0156853 | A1 | 6/2013 | Zhang et al. |
| 2013/0189316 | A1 | 7/2013 | Chen |

FOREIGN PATENT DOCUMENTS

| | | |
|---|---|---|
| CN | 101987199 A | 3/2011 |
| CN | 101926757 B | 1/2013 |
| EP | 1219304 B1 | 10/2004 |
| IN | 192711 A1 | 5/2004 |
| IN | 2003/MUM/2006 | 7/2008 |
| IN | 1758/MUM/2008 | 9/2008 |
| IN | 1382/MUM/2008 | 12/2009 |
| IN | 1548/MUM/2008 A | 7/2010 |
| IN | 2808/CHE/2009 | 2/2012 |
| IN | 295/DEL/2011 | 8/2012 |
| IN | 706/MUM/2010 | 11/2012 |
| IN | 3348/MUM/2012 | 12/2012 |
| KR | 10-2011-0037444 A | 4/2011 |
| WO | 9603121 A1 | 2/1996 |
| WO | 0006120 A1 | 2/2000 |
| WO | 2005/011600 A2 | 2/2005 |
| WO | 2006037089 A2 | 4/2006 |
| WO | 2006/095363 A2 | 9/2006 |
| WO | 2006096955 A1 | 9/2006 |
| WO | 2006/126214 A2 | 11/2006 |
| WO | 2008013822 A2 | 1/2008 |
| WO | 2008/095587 A1 | 8/2008 |
| WO | 2008/115572 A1 | 9/2008 |
| WO | 2009/089269 A1 | 7/2009 |
| WO | 2009/157010 A1 | 12/2009 |
| WO | 2011144650 A1 | 11/2011 |
| WO | 2012028101 A1 | 3/2012 |
| WO | 2012144678 A1 | 10/2012 |
| WO | 2013/013076 A1 | 1/2013 |
| WO | 2013/101749 A1 | 7/2013 |

OTHER PUBLICATIONS

Klang< "PFAT5 and the Evolution of Lip[id Admixture Stability" in Journal of Parenteral and Enteral Nutritrion, Sep. 2015.*
International Search Report from International Publication No. PCT/US2014/030519 dated May 28, 2014.
International Journal of Clinical Pharmacology and Therapeutics (2012), 50(6), 383-390, Zeitlinger, Markus; Rusca, Antonio; Oraha, Alhan Z.; Gugliotta, Barbara; Mueller, Markus; Ducharme, Murray P.
PDA Journal of Pharmaceutical Science and Technology (2012), 66(1), 28-37, Ramreddy, Srividya; Kandadi, Prabhakar; Veerabrahma, Kishan.
International Journal of Pharmacy and Pharmaceutical Sciences (2011), 3(Suppl.5), 250-252, Bhatt, Krunal; Patel, Priyal R.
Tap Chi Duoc Hoc (2010), 50(11), 10-14, Cao, Ngoc Anh; Chi, Sang-Cheol (Abstract only)(English Abstract Only).
Acute Pain (2009), 11(1), 15-21, Colucci, Robert D.; Wright, Curtis, IV; Mermelstein, Fred H.; Gawarecki, Daniel G.; Carr, Daniel B.
Zhongguo Xinyao Zazhi (2003), 12(12), 1018-1021, Xie, Jun; Zhou, Jian-ping; Huang, Chun-yu (English Abstract only).
Tap Chi Duoc Hoc (2003), (3), 23-27 Nguyen, Dang Hoa; Nguyen, Van Long; Le, Thi Thu Hoai; Vu, Ngoc Uyen (English Summary Only).
Ong et al. (2007), An Evidence-Based Update on Nonsteroidal Anti-Inflammatory Drugs, Clinical Medicine & Research; vol. 5, No. 1:19-34.
Strickley, Solubilizing Excipients in Oral and Injectable Formulations, Pharmaceutical Research, vol. 21, No. 2, Feb. 2004; p. 201-230.
Patel et al., Phospholipid-Based Microemulsions Suitable for Use in Foods, J. Agric. Food Chem. 2006, 54, 7817-7824.

* cited by examiner

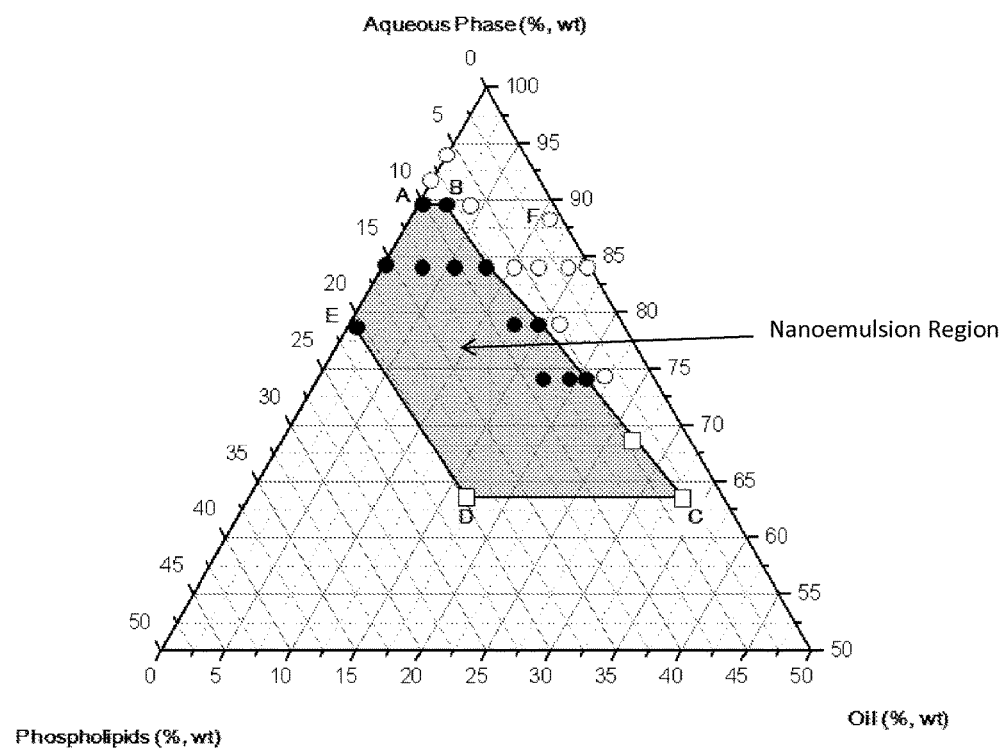
FIGURE 1: Phase diagram depicting a "nanoemulsion region" (grey area), which is defined by connecting lines between five compositions (A, B, C, D and E).

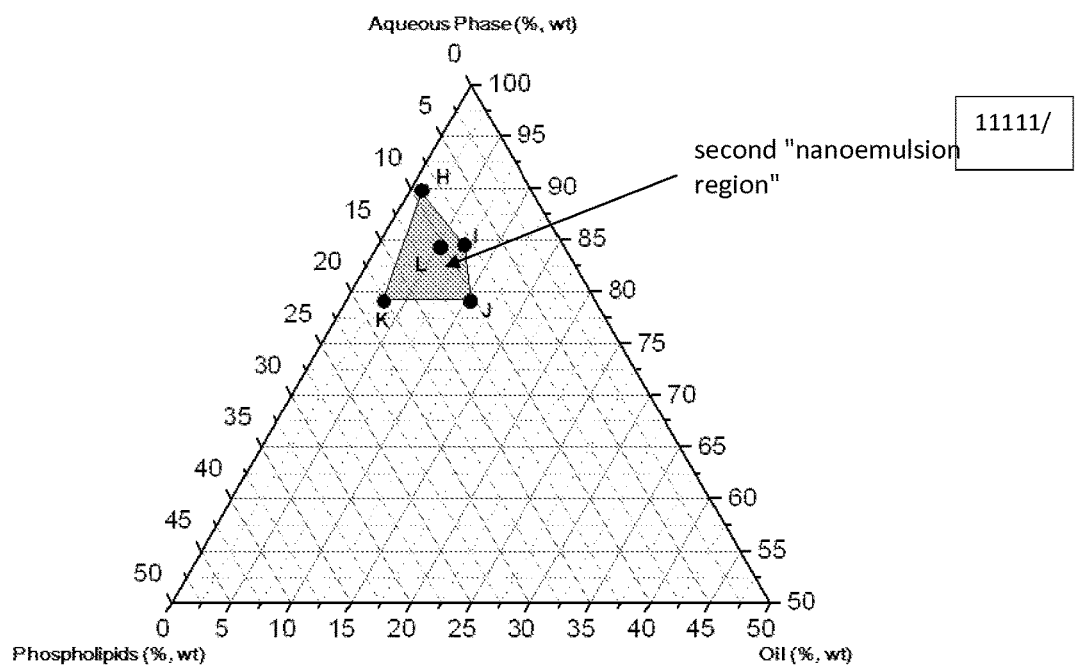
FIGURE 2: Phase diagram depicting a second "nanoemulsion region" region (grey area), which is defined by connecting lines between five critical compositions (H, I, J, and K).

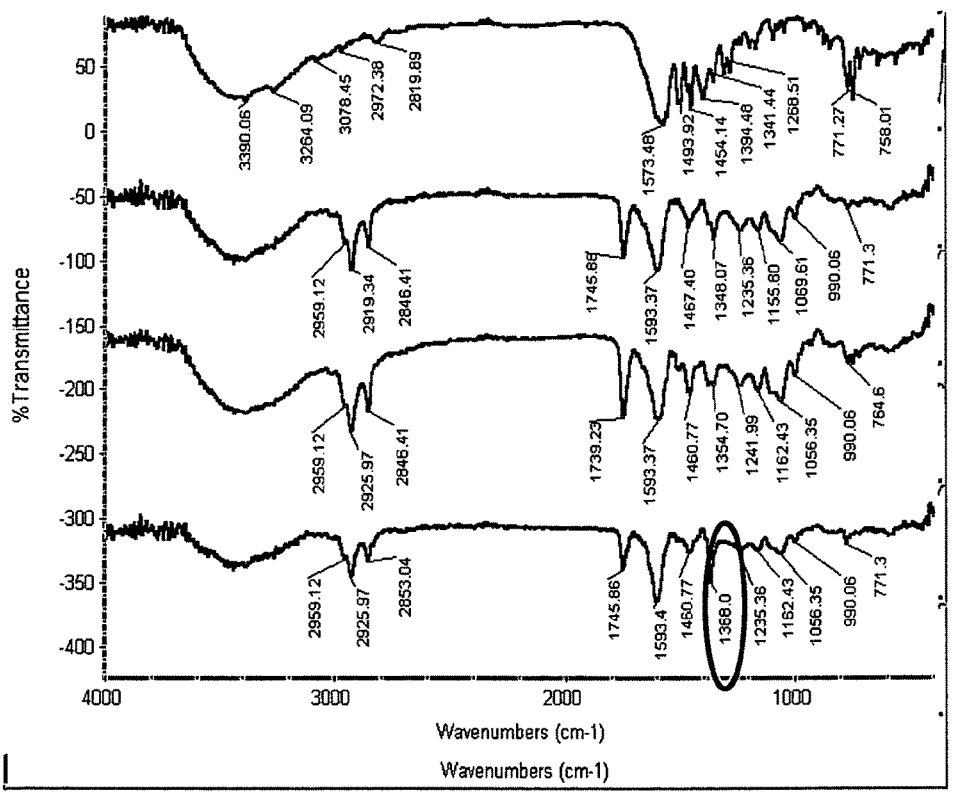
Figure 3: From top to bottom are IR spectra of diclofenac sodium, dried Example 21 Vehicle, Physical Mixture and dried Example 21.

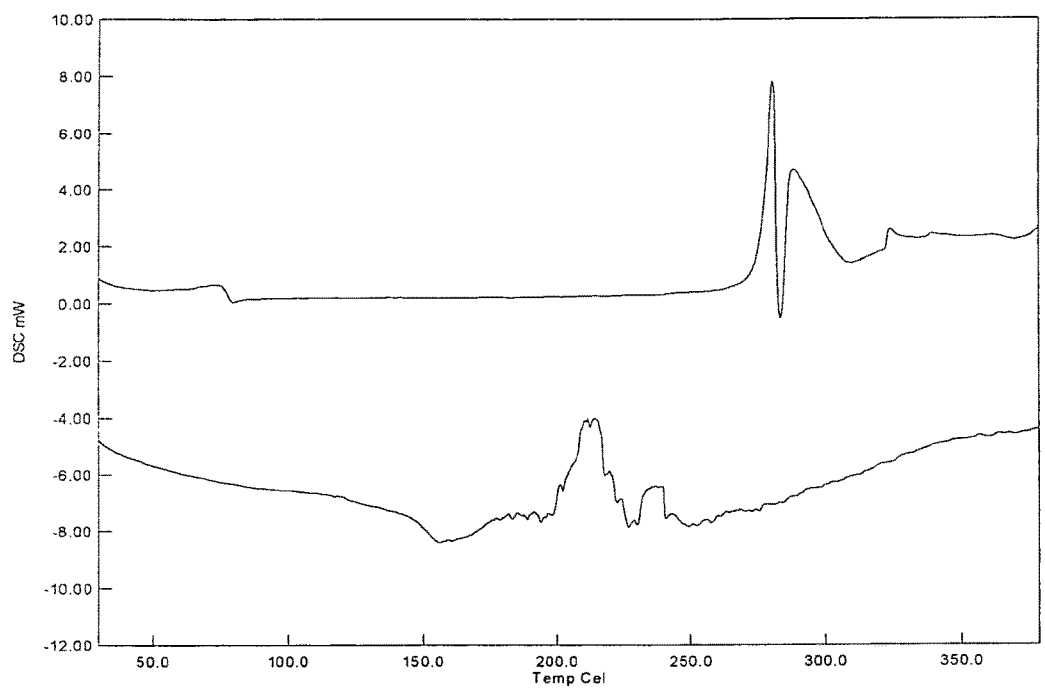
FIGURE 4: DSC thermograms of diclofenac sodium (upper) and the dried Example 21 (lower).

PARENTERAL DICLOFENAC COMPOSITION

CROSS-REFERENCE TO RELATED APPLICATIONS

The present application is a national phase entry under 35 U.S.C. § 371 of International Application No. PCT/US2014/030519 filed on Mar. 17, 2014, which claims the priority from U.S. Provisional Application No. 61/793,356 filed Mar. 15, 2013, the disclosure of which are incorporated herein by reference.

FIELD OF THE INVENTION

The present invention relates to parenteral composition comprising diclofenac or a pharmaceutically acceptable salt. The present invention also provides methods for preparing and using such parenteral composition.

BACKGROUND

In postoperative pain management, health care professionals generally are required to administer opioids, which is a potent analgesic. Although opioids have proven pain management properties, they also have a significant number of potential side effects, including nausea, vomiting, constipation, pruritus, urinary retention, respiratory depression, and sedation. On the other hand non-steroidal, anti-inflammatory drugs (NSAIDs) provide anti-inflammatory and analgesic effects, but they are limited to oral or rectal administrations greatly limiting the use of NSAIDs under postoperative conditions. Currently, ketorolac tromethamine is only NSAID that can be administered intravenously or intramuscularly, but its chronic use is limited due to GI toxicity.

Diclofenac, chemical name o-(2,6-dichloroanilino)phenylacetic acid, is known as a potent analgesic and antirheumatic and is described, in U.S. Pat. No. 3,558,690. Diclofenac is sold commercially as immediate release, delayed release (enteric coated) and extended-release (sustained-release) dosage forms. Due to the relatively large "first-pass-effect" of the substance and for faster flooding it is desirable to use injection solutions, in which an amount of 75 mg should be used per injection. For intramuscular/intravenous injections, the volume is to be kept as low as possible.

Due to the relatively poor solubility of diclofenac in water an aqueous injection solution with a reasonable volume cannot be obtained. Further, diclofenac is relatively instable in solution.

Examples of Diclofenac injectable compositions known in the art are:

U.S. Pat. No. 4,593,044 to Merckle GmbH describes a ready-to-use injection solution with as high an active compound content as possible in a small volume. The solubilization of diclofenac is achieved by using lysinate salt form of diclofenac and solubilizers such as propylene glycol, glycerol or polyoxyalkylenes.

U.S. Pat. No. 5,283,067 to Ciba-Geigy Corporation describes a lyophilized formulation comprising micronized diclofenac sodium, which is meant for intramuscular injection. This lyophilized formulation, after being suspended in an aqueous liquid vehicle, is converted into a dosage form for parenteral administration.

U.S. Pat. No. 5,389,681 to Ciba-Geigy Corporation describes a sterilizable parenteral solution comprising a diclofenac salt and stabilizers, such as ethyl lactate combined with glutathione or N-acetylcysteine.

U.S. Pat. No. 7,422,028 to Ibsa Institut Biochemique S.A. discloses aqueous solution comprising a complex of diclofenac and hydroxypropyl-β-cyclodextrin in the molar ratio of 1:1 and 1:1.3. The composition further comprises polysorbate in lower concentration. See also U.S. Pat. Nos. 4,309,421, 4,711,906, and 5,693,337; and U.S. App. Nos. 2011/0200657, 2005/0058699, and 2013/0156853

Although several of above references disclose various diclofenac injectable compositions, there exists a long felt need to develop a stable composition that is ready-to-inject intramuscularly or intravenously and causes minimal irritation to the tissues at the site of the injection.

It has been challenging to design a stable diclofenac parenteral composition that can be readily administered (without dilution or forming suspension) to alleviate pain or inflammation, especially in unconscious/unresponsive patients. It has also been challenging to formulate a composition that minimizes GI ulceration or bleeding after surgery, and other concurrent damage to the GI membranes or layers.

The present inventors provided compositions meant for parenteral administration comprising diclofenac or its pharmaceutically acceptable salt to a subject that can be used in postoperative pain management, with minimal or no side-effects and which, in some embodiments, can meet one or more of these needs.

SUMMARY

The present application provides parenteral compositions of diclofenac or its pharmaceutically acceptable salt and methods for making and using such compositions.

Some of the compositions of the present application has one or more following properties: (1) ready to be injectable, (2) in the form of an oil-in-water emulsion, (3) stable under appropriate storage conditions, (4) containing therapeutically effective amount of diclofenac or its pharmaceutically acceptable salt, (5) sterilizable by filtration (6) containing components acceptable by regulatory agencies (e.g. the FDA), (7) containing low oil content and thus not exacerbating hyerlipidemia, and (8) is neither hyperallergenic nor vein irritating.

In one aspect, the present application provides a parenteral composition in the form of oil-in-water emulsion that comprises:
  (a) diclofenac or its pharmaceutically acceptable salt,
  (b) an oil component,
  (c) a phospholipid component, and
  (d) water.

In another aspect, the present application provides a parenteral composition comprising diclofenac sodium in an amount of 18.75 mg or 37.5 mg.

In one embodiment, the present application provides a parenteral composition in the form of oil-in-water emulsion that comprises:
  (a) diclofenac or its pharmaceutically acceptable salt,
  (b) an oil component,
  (c) a phospholipid component, and
  (d) water.

In one embodiment, the total concentration of the oil component is within a range of about 1% to about 50%, by weight. In some embodiments, the total concentration of the oil component is within a range of about 1% to about 20%, by weight. In further embodiments, the total concentration of the oil component is within a range of about 1% to about 10%, by weight. In still further embodiments, the total concentration of the oil component is within a range of about 1% to about 5%, by weight.

In one embodiment, the ratio of the oil component to phospholipid in the emulsions may range from about 1:20 to about 20:1 (w/w). In some embodiments, the ratio of the oil component to phospholipid in the emulsion may range from about 1:10 to about 10:1 (w/w). In some embodiments, the ratio of the oil component to phospholipid in the emulsion may range from about 1:5 to about 5:1 (w/w).

In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period of about 12 to about 24 months.

In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 1 month. In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 12 to about 24 months.

In one embodiment, the combined concentration of phospholipids and oil in the parenteral formulation is between about 10% to about 35% wt. Below 10% wt., the compositions are incapable of solubilizing diclofenac sodium to the desired concentration (e.g. 3.75%). Above 35% wt., the nanoemulsion can be too viscous to produce and may have compromised stability.

In one embodiment, ready-to-use parenteral composition in the form of oil-in-water nanoemulsion that comprises about 5 to about 45 mg/mL diclofenac sodium or a pharmaceutically acceptable salt, a phospholipid component and an oil component, wherein
  (a) the pH of the composition is between about pH 7.0 and pH 8.6,
  (b) the combined concentration of phospholipid component and the oil component between about 10% and about 35% wt, and
  (c) the weight ratio of phospholipids-to-oil is from about 1.0:20.0 to about 20.0:1.0

In one embodiment parenteral composition in the form of oil-in-water emulsion that comprises a nanoemulsion composition, wherein the nanoemulsion composition falls within a nanoemulsion region of a phase diagram, as shown in FIG. 1), wherein boundaries of a stable nanoemulsion are defined by lines between the five compositions (A, B, C, D and E), wherein the five compositions comprise about 1% to about 4.5% w/w diclofenac and correspond to a weight % ratio of Phospholipids:Oil:Aqueous Phase of 10:greater than 0:86.25 for A, 8:2:86.25 for B, 3:32:61.25 for C, 18:17:61.25 for D and 20:greater than 0:76.25 for E.

In one embodiment, the composition of present application has an aqueous phase in a concentration between about 65% and about 90% of the total weight of the composition.

In one embodiment, the concentration of diclofenac or its pharmaceutically acceptable salt in present invention may be between about 0.5% and about 4.5% wt. Due to solubility limitation of diclofenac, precipitation may occur if the concentration of diclofenac is greater than 4.5% wt. However, if the diclofenac concentration is below 4.5%, a stable nanoemulsion of the current invention can be obtained.

The solubility of diclofenac in the nanoemulsion of present application is pH-dependent. Below pH 7.0, diclofenac precipitation can occur in the nanoemulsion. On the other hand, at pH above 9, significant degradation of phospholipids may take place, resulting in an unstable nanoemulsion. In one embodiment, the nanoemulsion of present application has a pH between about 7.0 and about 9.0.

In another embodiment the composition comprises an oil component which is a vegetable oil. In another embodiment the composition is selected from almond oil, borage oil, black currant seed oil, corn oil, safflower oil, soybean oil, sesame oil, cotton seed oil, peanut oil, olive oil, rapeseed oil, coconut oil, palm oil, canola oil, castor oil. In another embodiment, vegetable oil is soybean oil.

In one embodiment, the above composition further comprises a cryoprotectant. In another embodiment, above composition comprises a cryoprotectant which is sucrose.

In one embodiment, the above composition further comprises an antioxidant. In another embodiment, the above composition comprises and antioxidant which is sodium sulfite, sodium bisulfite, sodium metabisulfite, butylatedhydroxytoluene, butylatedhydroxyanisole or a mixture thereof.

In certain embodiments, the vegetable oil to medium chain triglyceride ratio in the oil-in-water emulsion can be within a range of about 9:1 to about 1:1, by weight. In certain embodiments, the ratio of the vegetable oil to MCT is about 9:1, 8:1, 7:1, 6:1, 5:1, 4:1, 3:1, 2:1 or 1:1. In some embodiments, the vegetable oil to medium chain triglyceride ratio in an oil-in-water emulsion is within the range of about 5:1 to about 1:1. In further embodiments, the vegetable oil to medium chain triglyceride ratio in an oil-in-water emulsion is about 1:1.

In one embodiment, the total concentration of the oil component is within a range of about 0% to about 50%, by weight. In certain embodiments, the total concentration of the oil component is about at most about 5%, 10%, 15%, 20%, 25%, 30%, 35%, 40%, 45%, or 50% by weight. In some embodiments, the total concentration of the oil component is within a range of about 1% to about 20%. In further embodiments, the total concentration of the oil component is within a range of about 1% to about 10%. In still further embodiments, the total concentration of the oil component is within a range of about 3% to about 7%.

In another aspect of this embodiment, the amount of phospholipids in the parenteral formulation, by weight is within a range of about 0.5% to about 20%. In some embodiments, the amount of phospholipids in the formulation, by weight, is within a range of about 1% to about 10%. In further embodiments, the amount of phospholipids in the formulation, by weight, is within a range of about 2% to about 5%.

In still another aspect of this embodiment, the ratio of the oil component to phospholipid in the emulsions may range from about 1:20 to about 20:1 (w/w). In some embodiments, the ratio of the oil component to phospholipid in the emulsion may range from about 1:10 to about 10:1 (w/w). In some embodiments, the ratio of the oil component to phospholipid in the emulsion may range from about 1:5 to about 5:1 (w/w).

In one aspect of this embodiment, the oil-in-water emulsions comprises about 1% to about 5% % w/w diclofenac, or a pharmaceutically acceptable salt thereof, about 0% to about 35% w/w of the oil component, about 1% to about 20% w/w of the phospholipid component, and about 60% to about 90% w/w of the aqueous component. The ratio of the oil component to phospholipid in the emulsions may range from about 1:20 to about 20:1 (w/w). Other times, the ratio of the oil component to phospholipid in the emulsion may range from about 1:10 to about 10:1 (w/w). The ratio of the oil component to phospholipid in the emulsion may also range from about 1:5 to about 5:1 (w/w).

Another way to characterize a particular subgroup of aspects of this embodiment is by defining the nanoemulsion using the boundaries of a phase diagram. In one aspect of this embodiment, the nanoemulsion composition falls within a second "nanoemulsion region" of a phase diagram, as shown in FIG. 2, wherein the boundaries of the second nanoemulsion region are defined by lines between the four compositions (H, I, J and K), wherein the four compositions comprises about 1% to about 5% % w/w diclofenac and correspond to a weight % ratio of Phospholipids:Oil:Aqueous Phase of 9:1:86.25 for H, 8:7:81.25 for I, 10:10:76.25 for J, and 17:3:76.25 for K.

In one aspect of this embodiment, the oil-in-water emulsions comprises about 1% to about 5% w/w diclofenac, or a pharmaceutically acceptable salt thereof, about 1% to about 12% w/w of the oil component, about 5% to about 20% w/w of the phospholipid component, and about 70% to about 90% w/w of the aqueous component, wherein the combined concentration of the phospholipid and oil components is about 10% to about 30% w/w. In another aspect of this embodiment, the ratio of the oil component to phospholipid in the emulsion may range from about 1:10 to about 10:1 (w/w). In a further aspect of this embodiment, the ratio of the oil component to phospholipid in the emulsion may range from about 1:5 to about 5:1 (w/w).

In certain embodiments, the average diameter of the droplets in the oil-in-water emulsions of the composition is from about 20 to about 250 nm. In certain embodiments, the average diameter of the oil droplets may be within a range of about 50 to about 200 nm. In other embodiments, the average diameter of the oil droplets may be within a range of about 20 nm to about 150 nm. In certain embodiments, the average droplet diameter is about 50, 60, 70, 80, 90, 100, 110, 120, 130, 140, 150, 160, 170, 180, 190 or 200 nm.

In certain embodiments, the composition of the present application may be filter sterilized using via 0.2 µm filters. In certain embodiments, the composition of present application may be sterilized by autoclave methods.

In another aspect, the present application provides a parenteral composition of diclofenac or its pharmaceutically acceptable salt, wherein the composition provides $AUC_{(0-t)}$ (area under the concentration-time curve from time 0 to the time of last sample with a quantifiable concentration) of at least about 900 ng/mL*h.

In another aspect, the present application provides a parenteral composition of diclofenac or its pharmaceutically acceptable salt, wherein the composition provides $AUC_{(0-inf)}$ (area under the concentration-time curve from time 0 to infinity) of at least about 900 ng/mL*h.

In one embodiment, the composition displays an additional peak at about 1360 cm-1 to about 1370 cm-1 when a sample of the composition is placed in a KBr pellet and subjected to FT-IR analysis.

In one embodiment, the composition is substantially free of a thermal event when a sample of the composition is placed in a Differential Scanning calorimeter, wherein the sample is heated at the speed of 5° C./min from 30° C. to 380° C. under nitrogen gas.

In one embodiment, the emulsion may be prepared by the process comprising the steps of:
(a) forming a mixture that comprises appropriate amounts of
 (i) diclofenac or its pharmaceutically acceptable salt,
 (ii) an oil component (e.g., a vegetable oil, or a combination of a vegetable oil and a medium chain glyceride), and
 (iii) a phospholipid component, and
(b) forming an oil-in-water emulsion with the mixture of step (a) and an aqueous solution.

In certain embodiments, step (b) may be performed by adding the aqueous solution to the mixture of step (a) to form a primary emulsion. In some embodiments, the aqueous solution is water or a buffer solution, and may contain stabilizer(s) and/or tonicity modifier(s). In some embodiments, the formation of the primary emulsion may be performed or facilitated by the use of mechanical homogenization (e.g., high shear mixing, high pressure extrusion, and microfluidization) or other suitable techniques.

In some embodiments, the methods may further comprise one or more of the following steps: (A) combining all components in any order of addition, (B) mixing and homogenizing to dissolve diclofenac or its pharmaceutically acceptable salt and to provide an emulsion with a mean droplet diameter less than about 200 nm, and (C) sterilizing the emulsion by filtration using a 0.2 µm filter.

In some embodiments, the methods may further comprise one or more steps to adjust the pH of the emulsion to a desirable range, and such adjustment can take place at any step before or after the sterilization step.

In another aspect, the parenteral dosage form of diclofenac as per this application is prepared without utilizing any organic solvents or toxic solubilizers. In another embodiment, the parenteral dosage form of diclofenac or a pharmaceutically salt thereof is prepared without using propylene glycol, benzyl alcohol, ethanol, polysorbate, cremophor, bile salt, poloxamer or any reagent that has not been used in an FDA approved injectable drug dosage form, as of the filing date.

In one embodiment, the composition of present application provides methods of treating pain associated with spinal cord injuries, traumatic brain injuries, strokes, injuries to the peripheral nerves system, injuries to the central nerves systems or injuries to other systems having nerve tissue, preferably the injury has associated with it inflammation, where the methods include the step of administering a composition of this invention to an mammal including a human or directly to the site of injury or into the blood or other bodily fluid of the mammal including a human.

In another aspect, the present application provides a method of treating inflammation, pain and/or fever in a mammal, which comprises parenterally administering the aforesaid parenteral composition to the mammal.

BRIEF DESCRIPTION OF THE DRAWINGS

FIG. 1: Phase Diagram depicting a "nanoemulsion region"

FIG. 2: Phase Diagram depicting a second "nanoemulsion region"

FIG. 3: FT-IR Spectra of Diclofenac Sodium, dried Example 21 vehicle, Physical Mixture, and Dried Example 21

FIG. 4: DSC Thermogram of Diclofenac sodium and dried Example 21

DETAILED DESCRIPTION

While the specification concludes with the claims particularly pointing and distinctly claiming the invention, it is believed that the present invention will be better understood from the following description. The present invention can comprise (open ended) or consist essentially of the components of the present invention as well as other ingredients or elements described herein. As used herein, "comprising" is "open ended" and means the elements recited, or their equivalent in structure or function, plus any other element or elements which are not recited. The terms "having" and "including" are also to be construed as open ended unless the context suggests otherwise. All ranges recited herein include the endpoints, including those that recite a range "between" two values.

"Diclofenac" as used herein also encompasses pharmaceutically acceptable salts. The solid state form of diclofenac used in the composition of the present invention is not critical. For example, diclofenac can be amorphous or crystalline.

The term "pharmaceutically acceptable salts" as used herein includes those salts which are, within the scope of sound medical judgment, suitable for use in contact with the tissues of humans and lower animals without undue toxicity, irritation, allergic response and the like, which are well known in the art. The salts can be prepared in situ during the final isolation and purification of the compounds of the invention, or separately by reacting the pharmaceutically active substance having a free base function with a suitable organic acid or inorganic acid.

Examples of pharmaceutically acceptable nontoxic acid addition salts include, but not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange techniques. Other pharmaceutically acceptable salts include, but not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, diethylamine, ethanesulfonate, formate, fumarate, glucoheptonate, glycerophosphate, gluconate, hemisulfate, heptanoate, hexanoate, hydroiodide, 2-hydroxy-ethanesulfonate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartarate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The phrase 'therapeutically effective amount' as used herein, means an amount of diclofenac, sufficient to reduce the pain, but low enough to avoid serious side effects (at a reasonable benefit/risk ratio), within the scope of sound medical judgment. The effective amount of the diclofenac will vary with the particular condition being treated, the age and physical condition of the patient being treated, the severity of the condition, the duration of the treatment, the nature of concurrent therapy, and like factors within the knowledge and expertise of the attending physician. Unless otherwise specified, amounts indicated herein reflect the amount based on the weight of free diclofenac. Amounts are by weight unless specified expressly or by context.

The terms such as "about", "up to", "generally", "substantially" and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value.

$AUC_{(0-t)}$ represents area under the concentration-time curve from time 0 to the time of last sample with a quantifiable concentration.

$AUC_{(0-inf)}$ represents area under the concentration-time curve from time 0 to infinity.

The term "oil-in-water emulsion" as used herein, refers to a colloidal dispersion system in which liquid oil is dispersed in small droplets (the discrete phase, also referred to as "the oil phase") in an aqueous medium (the continuous phase, also referred to as "the aqueous phase"), wherein in excess of 80% of the drug is dissolved and remains in the oil droplets. In certain embodiments, greater than 85%, 90%, 95% or 99% of the drug is present in the oil phase.

The term "oil-in-water nanoemulsion" or "nanoemulsion" as used herein, refers to a colloidal dispersion system in which liquid oil is dispersed in an aqueous medium, wherein the average diameter of the droplets ranges from about 20 to about 250 nm. In certain embodiments, the average diameter of the oil droplets may be within a range of about 50 to about 200 nm. In other embodiments, the average diameter of the oil droplets may be within a range of about 20 nm to about 150 nm. In certain embodiments, the average droplet diameter is about 50, 60, 70, 80, 90, 100, 110, 120, 130, 140, 150, 160, 170, 180, 190 or 200 nm.

The term "oil" as used herein, means a general sense to identify hydrocarbon derivatives, carbohydrate derivatives, or similar organic compounds that are liquid at body temperatures, e.g., about 37° C., and are pharmacologically acceptable in injectable compositions. It includes glycerides or non-glycerides.

The term "oil component" or "oil phase" refers to an oil, or a combination of multiple oils.

In certain embodiments, the oil component of the present application comprises a monoglyceride, a diglyceride, a triglyceride, or a mixture thereof. In certain embodiments, the oil component comprises an ester formed between one or more fatty acids and an alcohol other than glycerol.

In certain embodiments, the oil refers to a "vegetable oil". Vegetable oil refers to oil derived from plant seeds or nuts. Exemplary vegetable oils include, but are not limited to, almond oil, borage oil, black currant seed oil, corn oil, safflower oil, soybean oil, sesame oil, cottonseed oil, peanut oil, olive oil, rapeseed oil, coconut oil, palm oil, canola oil, castor oil, etc. Vegetable oils are typically "long-chain triglycerides," formed when three fatty acids (usually about 14 to about 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are generally used to ensure safety and stability of oil-in-water emulsions. In certain embodiments, hydrogenated vegetable oils, which are produced by controlled hydrogenation of the vegetable oil.

In some embodiments, the oil refers to "medium chain triglycerides". Medium chain triglycerides (MCl's) are another class of triglyceride oil that can be either naturally derived or synthetic. MCT's are made from fatty acids that are usually about 8 to about 12 carbons in length. Like vegetable oils, MCT's have been used extensively in emulsions designed for injection. Such oil is commercially available as Miglyol 812 from SASOL GmbH, Germany, CRODAMOL GTCC-PN from Croda Inc. of Parsippany, N.J., or Neobees M-5 oil from PVO International, Inc., of Boonton, N.J. Other low-melting medium chain oils may also be used in the present invention.

In one embodiment, the oil component refers to one or more oil. In some embodiments, the oil encompasses one or more medium chain mono- or di- or tri-glycerides. In some embodiments, the oil encompasses mixture of one or more oil and one or more medium chain mono- or di- or tri-glyceride. In further embodiments, the oil comprises a mixture of one or more oils and one or more long chain mono- or di- or tri-glycerides.

In some embodiments, the medium chain glyceride refers to medium chain mono- or di- or tri-glyceride. In some embodiments, the medium chain glyceride comprises a mixture of one or more medium chain mono- or di- or tri-glycerides.

In one embodiment, the phospholipid refers to one or more phospholipids.

In one embodiment, the parenteral composition comprises of diclofenac or its pharmaceutically acceptable salts thereof from about 5 mg/ml to about 45 mg/ml. In some embodiments, parenteral composition comprises of diclofenac or its pharmaceutically acceptable salts thereof from about 10 mg/ml to about 40 mg/ml.

An "emulsifier" refers to a compound that reduces the separation of the injectable emulsion into individual oil and aqueous phases. Emulsifiers useful in the present invention generally are (1) compatible with the other ingredients of the oil-in-water emulsions of the present invention, (2) do not interfere with the stability or efficacy of the diclofenac in the emulsions, (3) are stable and does not deteriorate in the preparation, and (4) are non-toxic.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax based emulsifiers, glycerol monostearate, glycerine sorbitan fatty acid esters and phospholipids.

A "phospholipid" refers to a ester of glycerol with at least one fatty acid and at least one phosphate group. Exemplary phospholipids useful in the present invention include, but are not limited to, phosphatidyl choline, lecithin (a mixture of choline ester of phosphorylated diacylglyceride), phosphatidyl ethanolamine, phosphatidyl glycerol, phosphatidic acid with about 4 to about 22 carbon atoms, and more generally from about 10 to about 18 carbon atoms and varying degrees of saturation. The phospholipid component of the drug delivery composition can be either a single phospholipid or a mixture of several phospholipids. The phospholipids should be acceptable for the chosen route of administration.

The 'phospholipids' can be of natural origin or synthesized.

Naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have a long history of safety, possess combined emulsification and solubilization properties, and tend to be broken down into innocuous substances more rapidly than most synthetic surfactants. Commercially available soya phospholipids are the CENTROPHASE and CENTROLEX products marketed and sold by Central Soya, PHOSPHOLIPON from Phospholipid GmbH, Germany, LIPOID by Lipoid GmbH, Germany, and EPIKURON by Degussa.

Phospholipids can also be synthesized. Exemplary common synthetic phospholipids include, but not limited to Diacylglycerols such as 1,2-Dilauroyl-sn-glycerol (DLG), 1,2-Dimyristoyl-sn-glycerol (DMG), 1,2-Dipalmitoyl-sn-glycerol (DPG), 1,2-Distearoyl-sn-glycerol (DSG); Phosphatidic Acids such as 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt (DSPA,Na); Phosphocholines such as 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Dipalmitoyl-sn-glycero-3-phosphocholine (DPPC), 1,2-Distearoyl-sn-glycero-3-phosphocholine (DSPC), 1,2-Distearoyl-sn-glycero-3-phosphocholine (DSPC); Phosphoethanolamines such as 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); Phosphoglycerols such as 1,2-Dilauroyl-sn-glycero-3-phosphoglycerol, sodium salt (DLPG), 1,2-Dimyristoyl-sn-glycero-3-phosphoglycerol, sodium salt (DMPG), 1,2-Dimyristoyl-sn-glycero-3-phospho-sn-1-glycerol, ammonium salt (DMP-sn-1-G,NH$_4$), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na); Phosphoserines such as 1,2-Dipalmitoyl-sn-glycero-3-phospho-L-serine, sodium salt (DPPS,Na); Mixed Chain Phospholipids such as 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt POPG,NH$_4$); Lysophospholipids such as 1-Palmitoyl-2-lyso-sn-glycero-3-phosphocholine (P-lyso-PC), 1-Stearoyl-2-lyso-sn-glycero-3-phosphocholine (S-lyso-PC); Pegylated Phospholipids such as N-(Carbonyl-methoxypolyethyleneglycol 2000)-MPEG-2000-DPPE, 1,2-dipalmitoyl-sn-glycero-3-phosphoethanolamine, sodium salt, N-(Carbonyl-methoxypolyethyleneglycol 5000)-MPEG-5000-DSPE, 1,2-distearoyl-sn-glycero-3-phosphoethanolamine, sodium salt, N-(Carbonyl-methoxypolyethyleneglycol 5000)-MPEG-5000-DPPE, 1,2-dipalmitoyl-sn-glycero-3-phosphoethanolamine, sodium salt, N-(Carbonyl-methoxypolyethyleneglycol 750)-MPEG-750-DSPE, 1,2-distearoyl-sn-glycero-3-phosphoethanolamine, sodium salt, N-(Carbonyl-methoxypolyethyleneglycol 2000)-MPEG-2000-DSPE, 1,2-distearoyl-sn-glycero-3-phosphoethanolamine, sodium salt.

The term "mammal" is defined as any class of warm-blooded higher vertebrates that includes humans.

In one embodiment, the present application provides a parenteral composition in the form of oil-in-water emulsion that comprises:
(a) diclofenac or its pharmaceutically acceptable salt,
(b) an oil component,
(c) a phospholipid component, and
(d) water.

In one embodiment, the total concentration of the oil component is within a range of about 1% to about 50%, by weight. In some embodiments, the total concentration of the oil component is within a range of about 1% to about 20%, by weight. In further embodiments, the total concentration of the oil component is within a range of about 1% to about 10%, by weight. In still further embodiments, the total concentration of the oil component is within a range of about 1% to about 5%.

In one embodiment, the ratio of the oil component to phospholipid in the emulsions may range from about 1:20 to about 20:1 (w/w). In some embodiments, the ratio of the oil component to phospholipid in the emulsion may range from about 1:10 to about 10:1 (w/w). In some embodiments, the ratio of the oil component to phospholipid in the emulsion may range from about 1:5 to about 5:1 (w/w).

In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period of about 12 to about 24 months.

In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 1 month. In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 12 to about 24 months.

In one embodiment of the above aspect, the present application relates to a parenteral composition in the form of oil-in-water emulsion that comprises:
(a) diclofenac or its pharmaceutically acceptable salt,
(b) a medium chain triglyceride,
(c) one or more phospholipids, and
(d) water.

In one embodiment, the total concentration of the medium chain triglyceride component is within a range of about greater than 0% to about 50%, by weight. In some embodiments, the total concentration of the medium chain triglyceride component is within a range of about 1% to about 20%, by weight. In further embodiments, the total concentration of the medium chain triglyceride component is within a range of about 1% to about 10%, by weight. In still further embodiments, the total concentration of the medium chain triglyceride component is within a range of about 1% to about 5%, by weight.

In one embodiment, the ratio of the medium chain triglyceride component to phospholipid in the emulsions may range from about 1:20 to about 20:1 (w/w). In some embodiments, the ratio of the medium chain triglyceride component to phospholipid in the emulsion may range from about 1:10 to about 10:1 (w/w). In some embodiments, the ratio of the medium chain triglyceride component to phospholipid in the emulsion may range from about 1:5 to about 5:1 (w/w).

In another aspect, the present application provides a parenteral composition in the form of oil-in-water emulsion that comprises:
(a) diclofenac or its pharmaceutically acceptable salt,
(b) an oil component,
(c) a phospholipid component,
(d) at least one tonicity modifying agent, and
(e) water.

In one embodiment, the total concentration of the oil component is within a range of about 0% to about 50%, by weight. In some embodiments, the total concentration of the oil component is within a range of about 1% to about 20%, by weight. In further embodiments, the total concentration of the oil component is within a range of about 1% to about 10%, by weight. In still further embodiments, the total concentration of the oil component is within a range of about 1% to about 5%, by weight.

In one embodiment, the ratio of the oil component to phospholipid in the emulsions may range from about 1:20 to about 20:1 (w/w). In some embodiments, the ratio of the oil component to phospholipid in the emulsion may range from about 1:10 to about 10:1 (w/w). In some embodiments, the ratio of the oil component to phospholipid in the emulsion may range from about 1:5 to about 5:1 (w/w).

In another embodiment, the present application provides a parenteral composition in the form of oil-in-water emulsion that comprises:
(a) diclofenac or its pharmaceutically acceptable salt,
(b) medium chain triglycerides (MCT),
(c) a phospholipid component,
(d) a cryoprotectant,
(d) at least one tonicity modifying agent, and
(e) water.

In one embodiment of the present application, medium chain triglyceride is selected from Miglyol 812.

In one embodiment, the total concentration of the medium chain triglyceride component is within a range of about 0% to about 50%, by weight. In some embodiments, the total concentration of the medium chain triglyceride component is within a range of about 1% to about 20%, by weight. In further embodiments, the total concentration of the medium chain triglyceride component is within a range of about 1% to about 10%, by weight. In still further embodiments, the total concentration of the medium chain triglyceride component is within a range of about 1% to about 5%, by weight.

In one embodiment, the combined concentration of phospholipids and oil in the parenteral formulation is between about 10% to about 35% wt. Below 10% wt., the compositions are incapable of solubilizing diclofenac sodium to the desired concentration (e.g. 3.75%). Above 35% wt., the nanoemulsion can be too viscous to produce and may have compromised stability.

In one embodiment, the weight ratio of phospholipids-to-oil in the parenteral formulation is not less than certain values, which depends on the combined concentration of phospholipids and oil as follows:

| Combined concentration of phospholipids and oils (% wt) | Minimal wt. ratio of phospholipids-to-oil |
|---|---|
| About 10 | 4:1 |
| About 15 | 1:1 |
| About 20 | 0.43:1 |
| About 25 | 0.25:1 |

In one embodiment, ready-to-use parenteral composition in the form of oil-in-water nanoemulsion that comprises about 5 mg/mL to about 45 mg/mL diclofenac sodium or a pharmaceutically acceptable salt, a phospholipid component and an oil component, wherein
 (a) the pH of the composition is between about pH 7.0 and pH 8.6,
 (b) the combined concentration of phospholipid component and the oil component between about 10% wt and about 35% wt, and
 (c) the weight ratio of phospholipids-to-oil is from about 1.0:20.0 to about 20.0:1.0

In one embodiment, ready-to-use parenteral composition in the form of oil-in-water nanoemulsion that comprises about 5 to about 45 mg/mL diclofenac sodium or a pharmaceutically acceptable salt, a phospholipid component and an oil component, wherein
 (a) The pH of the composition is between about pH 7.0 and pH 8.6,
 (b) The combined concentration of phospholipid component and the oil component is between about 10% wt and about 35% wt, and
 (c) The weight ratio of phospholipids-to-oil is not less than the following values depending upon the combined concentration of the phospholipid and oil components:

| Phospholipids-to-oil wt ratio value | Combined concentration of phospholipid and oil components (% wt) |
|---|---|
| 4:1 | About 10 |
| 1:1 | About 15 |
| 0.43:1 | About 20 |
| 0.25:1 | About 25 |

In one embodiment, a ready-to-use, chemically stable and physically parenteral composition in the form of oil-in-water nanoemulsion that comprises about 37.5 mg/mL diclofenac sodium or a pharmaceutically acceptable salt, a lecithin and an medium chain triglyceride, wherein
 (a) the pH of the composition is between about pH 7.0 and pH 8.6,
 (b) a combined concentration of lecithin and medium chain triglyceride is between about 10% and about 20% wt.
 (c) medium chain triglyceride concentration is between about 1% and about 10% wt.
 (d) lecithin concentration is between about 8% and about 17% wt.,
 (e) the weight ratio of lecithin-to-medium chain triglyceride is between about 1:1 and about 9:1, and
 wherein the composition has a mean oil droplet diameter less than 200 nm and an osmolality of less than about 300 mOsm.

In one embodiment parenteral composition in the form of oil-in-water emulsion that comprises a nanoemulsion composition, wherein the nanoemulsion composition falls within a nanoemulsion region of a phase diagram, as shown in FIG. 1, wherein boundaries of a stable nanoemulsion are defined by lines between the five compositions (A, B, C, D and E), wherein the five compositions comprise about 1% to about 4.5% % w/w diclofenac and correspond to a weight % ratio of Phospholipids:Oil:Aqueous Phase of 10:greater than 0:86.25 for A, 8:2:86.25 for B, 3:32:61.25 for C, 18:17:61.25 for D and 20:greater than 0:76.25 for E.

In one embodiment, the composition of present application has an aqueous phase in a concentration between about 65% and about 90% of the total weight of the composition.

In one embodiment, the concentration of diclofenac or its pharmaceutically acceptable salt in presented invention may be between about 0.5% and about 4.5% wt. Due to solubility limitation of diclofenac, precipitation may occur if the concentration of diclofenac is greater than 4.5% wt. However, if the diclofenac concentration is below 4.5%, a stable nanoemulsion of the current invention can be obtained.

In one embodiment, the present application provides a parenteral composition containing diclofenac or its pharmaceutically acceptable salt at about 0.5%, 1%, 1.5%, 2%, 2.5%, 3%, 3.25%, 3.5%, 3.75%, 4%, 4.25%, or 4.5% by weight, or at about 5 mg/mL, 10 mg/mL, 15 mg/mL, 20 mg/mL, 25 mg/mL, 30 mg/mL, 32.5 mg/mL, 35 mg/mL, 37.5 mg/mL, 40 mg/mL, 42.5 mg/mL or 45 mg/mL.

In one embodiment, the nanoemulsion of present application has a density about 1 g/mL.

The solubility of diclofenac in the nanoemulsion of present application is pH-dependent. Below pH 7.0, diclofenac precipitation can occur in the nanoemulsion. On the other hand, at pH above 9, significant degradation of phospholipids may take place, resulting in an unstable nanoemulsion. In one embodiment, the nanoemulsion of present application has a pH between about 7.0 and about 9.0.

In another embodiment, the nanoemulsion of present application has a pH at about between about 7.2, 7.3, 7.4, 7.5, 7.6, 7.7, 7.8, 7.9, 8.0, 8.1, 8.2, 8.3, 8.4, 8.5 or 8.6.

In another embodiment of the present application, a phospholipid is selected from Egg lecithin (e.g. LIPOID E-80) or Soy lecithin (e.g. LIPOID 5-100).

In another embodiment the composition comprises an oil component which is a vegetable oil. In another embodiment the composition is selected from almond oil, borage oil, black currant seed oil, corn oil, safflower oil, soybean oil, sesame oil, cotton seed oil, peanut oil, olive oil, rapeseed oil, coconut oil, palm oil, canola oil, castor oil. In another embodiment, vegetable oil is soybean oil.

In another embodiment, the present application provides a parenteral composition in the form of oil-in-water emulsion that comprises:
 (a) diclofenac sodium,
 (b) medium chain triglyceride,
 (c) Egg lecithin,
 (d) EDTA disodium dehydrate USP, and
 (e) water.

In one embodiment, the above composition further comprises a cryoprotectant. In another embodiment, above composition comprises a cryoprotectant which is sucrose.

In one embodiment, the above composition further comprises an antioxidant. In another embodiment, the above composition comprises and antioxidant which is sodium sulfite, sodium bisulfite, sodium metabisulfite, butylatedhydroxytoluene, butylatedhydroxyanisole or a mixture thereof.

In one embodiment, the total concentration of the MIGLYOL 812 component is within a range of about greater than 0% to about 50%, by weight. In some embodiments, the total concentration of the oil component is within a range of about 1% to about 20%. In further embodiments, the total concentration of the MIGLYOL 812 component is within a range of about 1% to about 10%. In still further embodiments, the total concentration of the MIGLYOL 812 component is within a range of about 1% to about 5%.

In one embodiment, the ratio of the MIGLYOL 812 component to phospholipid in the emulsions may range from about 1:20 to about 20:1 (w/w). In some embodiments, the ratio of the MIGLYOL 812 component to phospholipid in the emulsion may range from about 1:10 to about 10:1 (w/w). In some embodiments, the ratio of the MIGLYOL 812 component to phospholipid in the emulsion may range from about 1:5 to about 5:1 (w/w).

In another aspect, the present application provides a parenteral composition in the form of oil-in-water emulsion that comprises:
  (a) diclofenac sodium,
  (b) MIGLYOL 812,
  (c) Soy lecithin,
  (d) EDTA disodium dehydrate USP, and
  (e) water.

In one embodiment, the above composition further comprises a cryoprotectant. In another embodiment, the above composition further comprises a cryoprotectant which is sucrose.

In one embodiment, the total concentration of the medium chain triglyceride component is within a range of about 0% to about 50%, by weight. In some embodiments, the total concentration of the medium chain triglyceride component is within a range of about 1% to about 20%, by weight. In further embodiments, the total concentration of the medium chain triglyceride component is within a range of about 1% to about 10%, by weight. In still further embodiments, the total concentration of the medium chain triglyceride component is within a range of about 1% to about 5%, by weight.

In one embodiment, the ratio of the MIGLYOL 812 component to phospholipid in the emulsions may range from about 1:20 to about 20:1 (w/w). In some embodiments, the ratio of the MIGLYOL 812 component to phospholipid in the emulsion may range from about 1:10 to about 10:1 (w/w). In some embodiments, the ratio of the MIGLYOL 812 component to phospholipid in the emulsion may range from about 1:5 to about 5:1 (w/w).

In another embodiment, the present application relates to a parenteral composition in the form of oil-in-water emulsion that comprises:
  (a) diclofenac or its pharmaceutically acceptable salt,
  (b) an oil component comprising at least one vegetable oil and/or at least one medium chain triglyceride (MCT),
  (c) one or more phospholipids, and
  (d) water;
wherein the emulsion is chemically and physically stable.

In one aspect of this embodiment, the specific type of vegetable oil used (i.e., soy bean oil, corn oil, or safflower oil, etc.) is not critical, so long as it is safe, well tolerated, pharmaceutically acceptable, chemically stable and provides emulsion droplets having a desired size range.

In certain embodiments, the vegetable oil to medium chain triglyceride ratio in the oil-in-water emulsion can be within a range of about 9:1 to about 1:1, by weight. In certain embodiments, the ratio of the vegetable oil to MCT oil is about 9:1, 8:1, 7:1, 6:1, 5:1, 4:1, 3:1, 2:1 or 1:1. In some embodiments, the vegetable oil to medium chain triglyceride ratio in an oil-in-water emulsion is within the range of about 5:1 to about 1:1. In further embodiments, the vegetable oil to medium chain triglyceride ratio in an oil-in-water emulsion is about 1:1. In one embodiment, the total concentration of the oil component is within a range of about 0% to about 50%, by weight. In certain embodiments, the total concentration of the oil component is about at most about 5%, 10%, 15%, 20%, 25%, 30%, 35%, 40%, 45%, or 50% by weight. In some embodiments, the total concentration of the oil component is within a range of about 1% to about 20%. In further embodiments, the total concentration of the oil component is within a range of about 1% to about 10%. In still further embodiments, the total concentration of the oil component is within a range of about 3% to about 7%.

In another aspect of this embodiment, the amount of phospholipids in the parenteral formulation, by weight is within a range of about 0.5% to about 20%. In some embodiments, the amount of phospholipids in the formulation, by weight, is within a range of about 1% to about 10%. In further embodiments, the amount of phospholipids in the formulation, by weight, is within a range of about 2% to about 5%.

In still another aspect of this embodiment, the ratio of the oil component to phospholipid in the emulsions may range from about 1:20 to about 20:1 (w/w). In some embodiments, the ratio of the oil component to phospholipid in the emulsion may range from about 1:10 to about 10:1 (w/w). In some embodiments, the ratio of the oil component to phospholipid in the emulsion may range from about 1:5 to about 5:1 (w/w).

Another way to characterize aspects of this embodiment is by defining the nanoemulsion using the boundaries of a phase diagram, as shown in FIG. 1. In one aspect of this embodiment, the nanoemulsion composition falls within the "nanoemulsion region" of a phase diagram, wherein the boundaries of the nanoemulsion region are defined by lines between five compositions (A, B, C, D and E), wherein the five composition comprises about 1% to about 5% % w/w diclofenac and correspond to a weight % ratio of Phospholipids:Oil:Aqueous Phase of 10:0:86.25 for A, 8:2:86.25 for B, 3:32:61.25 for C, 18:17:61.25 for D and 20:0:76.25 for E. Note that there must be at least some oil present. The phase diagram illustrates the boundaries when oil=0, not the formulation of the invention.

In one aspect of this embodiment, the oil-in-water emulsions comprises about 1% to about 5% % w/w diclofenac, or a pharmaceutically acceptable salt thereof, about 0% to about 35% w/w of the oil component, about 1% to about 20% w/w of the phospholipid component, and about 60% to about 90% w/w of the aqueous component. The ratio of the oil component to phospholipid in the emulsions may range from about 1:20 to about 20:1 (w/w). Other times, the ratio of the oil component to phospholipid in the emulsion may range from about 1:10 to about 10:1 (w/w). The ratio of the oil component to phospholipid in the emulsion may also range from about 1:5 to about 5:1 (w/w). These embodiments are "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 25° C. for a period of about 24 months. These embodiments are also "physically stable" if the emulsion remains precipitate-free, and maintains a mean oil droplet diameter less than 200 nm and a PFAT5 less than 0.05% when stored at a temperature of about 25° C. for about 1 month. In some embodiments, the nanoemulsion is "physically stable" if it remains precipitate-free, and maintains a mean oil droplet diameter less than 200 nm and a PFAT5 less than 0.05% when stored at a temperature of about 25° C. for about 24 months.

Another way to characterize a particular subgroup of aspects of this embodiment is by defining the nanoemulsion using the boundaries of a ternary phase diagram, as shown in FIG. 2. In one aspect of this embodiment, the nanoemulsion composition falls within a second "nanoemulsion region" of a phase diagram, wherein the boundaries of the second nanoemulsion region are defined by lines between the four compositions (H, 1, J and K), wherein the four compositions comprises about 1% to about 5% % w/w diclofenac and correspond to a weight % ratio of Phospholipids:Oil:Aqueous Phase of 9:1:86.25 for H, 8:7:81.25 for I, 10:10:76.25 for J, and 17:3:76.25 for K.

In one aspect of this embodiment, the oil-in-water emulsions comprises about 1% to about 5% w/w diclofenac, or a pharmaceutically acceptable salt thereof, about 1% to about 12% w/w of the oil component, about 5% to about 20% w/w of the phospholipid component, and about 70% to about 90% w/w of the aqueous component, wherein the combined concentration of the phospholipid and oil components is about 10% to about 30% w/w. In another aspect of this embodiment, the ratio of the oil component to phospholipid in the emulsion may range from about 1:10 to about 10:1 (w/w). In a further aspect of this embodiment, the ratio of the oil component to phospholipid in the emulsion may range from about 1:5 to about 5:1 (w/w). The composition is "chemically stable" meaning that the diclofenac or its pharmaceutically acceptable salt in the composition is maintained at a concentration of no less than 90% of the initial concentration of diclofenac when stored at a temperature of about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 25° C. for a period of about 24 months. The nanoemulsion is "physically stable" if it remains precipitate-free, and maintains a mean oil droplet diameter less than 200 nm and a PFAT5 less than 0.05% when stored at a temperature of about 25° C. for about 1 month. In further aspects of this embodiment, the nanoemulsion is "physically stable" if it remains precipitate-free, and maintains a mean oil droplet diameter less than 200 nm and a PFAT5 less than 0.05% when stored at a temperature of about 25° C. for about 24 months.

In one embodiment, the oil-in-water emulsions comprises about 1% to about 5% w/w diclofenac, or a pharmaceutically acceptable salt thereof, 5% w/w of medium chain triglycerides, about 10% w/w of lecithin, and about 70% to 80% w/w of the aqueous component. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period of about 12 to about 24 months. In some embodiments, the nanoemulsion is "physically stable" if it remains precipitate-free, and maintains a mean oil droplet diameter less than 200 nm and a PFAT5 less than 0.05% when stored at a temperature of about 2-8° C. or about 25° C. for about 1 month. In some embodiments, the nanoemulsion is "physically stable" if it remains precipitate-free, and maintains a mean oil droplet diameter less than 200 nm and a PFAT5 less than 0.05% when stored at a temperature of about 2-8° C. or about 25° C. for about 12 to about 24 months.

In certain embodiments, the oil-in-water emulsions comprise oil in an amount that does not adversely impact hyperlipidemia when administered to a subject.

In certain embodiments, the average diameter of the droplets in the oil-in-water emulsions of the composition is from about 20 to about 250 nm. In certain embodiments, the average diameter of the oil droplets may be within a range of about 50 to about 200 nm. In other embodiments, the average diameter of the oil droplets may be within a range of about 20 nm to about 150 nm. In certain embodiments, the average droplet diameter is about 50, 60, 70, 80, 90, 100, 110, 120, 130, 140, 150, 160, 170, 180, 190 or 200 nm.

Particle size, zeta potential and polydispersity index can be determined using various instruments. For example, particle size analyzer using laser light scattering such as Zetasizer™ apparatus available from Malvern Instruments Ltd.

In one embodiment, the parenteral composition of the present application has a polydispersity index of about less than 1.0. In another embodiment, the parenteral composition of the present application has a polydispersity index of about less than 0.8. In another embodiment, the parenteral composition of the present application has a polydispersity index of about less than 0.5.

In one embodiment, the parenteral composition of the present application has zeta potential in a range of about −50 mV to about +50 mV. In some embodiments, the parenteral composition of the present application has zeta potential in a range of about −30 mV to about +30 mV. In further embodiments, the parenteral composition of the present application has zeta potential in a range of about −20 mV to about +20 mV. In still further embodiments, the parenteral composition of the present application has zeta potential in a range of about −10 mV to about +10 mV.

In one embodiment, the pH of the composition of present application is generally from about 5 to about 10. In another embodiment, the pH of the composition of present application is generally from about 6 to about 8. In another embodiment the pH of the composition is from about 3.0 about 6.0. In a further embodiment, the pH of the composition of present application is from about 6.0 to about 7.0. In another embodiment the pH of the composition is from about 7.0 about 8.0. In a further embodiment, the pH of the composition of present application is from about 8.0 to about 9.0. In a further embodiment, the pH of the composition of present application is from about 7.6 to about 10.0.

In certain embodiments, the composition of the present application may be filter sterilized using via 0.2 μm filters.

The term "filter sterilized" means a composition that has passed through a filter having a pore size sufficiently small to result the composition free or substantially free of bacterial contaminants. Bacteria generally range in size from about 0.2 μm to about 600 μm, with most bacteria having a size in the range of about 1 μm to about 10 μm. Filters having pore size of about 0.22 μm or less are considered to produce sterile filtrates and are sufficiently small to result in a filter sterilized composition. Such filters and filter kits are available from Millipore Corporate, as well as other manufacturers.

In some embodiments, the compositions of the present invention may optionally contain additives such as acidifying, alkalizing, buffering, chelating, complexing and solubilizing agents, antioxidants and antimicrobial preservatives, suspending and/or viscosity modifying agents, tonicity modifying agents, and other biocompatible materials or therapeutic agents. Such agents generally are present in the aqueous phase of the emulsion and may all be used in conventional amounts. In certain embodiments, such additives assist in stabilizing the emulsion or the drug in the emulsion and in rendering the composition biocompatible.

Compounds useful for modifying osmolality of the emulsions of the present invention are referred to "tonicity agent", "tonicity modifiers," or "osmolality modifiers."

The tonicity agent maybe potassium or sodium chloride, trehalose, sucrose, sorbitol, glycerol, mannitol, polyethylene glycol, propylene glycol, albumin, amino acid and mixtures thereof. In further embodiments, the tonicity agent also increases viscosity. In still further embodiments, the viscosity increasing tonicity agent is sorbitol or sucrose. In certain embodiments, the aqueous phase has an osmolality of about 150 mOsm, which is achieved with an agent that also increases viscosity, such as sorbitol or sucrose.

In some embodiments, the aqueous phase has an osmolality, with or without tonicity agents, of about 300 mOsm (milliosmoles). In certain embodiments, the aqueous phase has an osmolality of about 250 mOsm is achieved with an agent that also increases viscosity, such as sorbitol or sucrose. In certain embodiments, the concentration of the tonicity modifying agent is sufficient for providing tonicity of at least about 150 mOsm.

In one embodiment the tonicity modifying agent is present in the range of about 1% to about 40% w/w. In another embodiment, the tonicity modifying agent is present in the range of about 2% to about 30% w/w. In another embodiment, the tonicity modifying agent is present in the range of about 5% to about 20% w/w.

"Antioxidants" used in this invention refers primarily to metal ion chelators and/or reducing agents that are safe to use in an injectable product. A metal ion chelator functions as an antioxidant by binding to metal ions and thereby reduces the catalytic effect of metal ion on the oxidation reaction of the drug, oil or phospholipid components. Metal chelators useful in this invention include, but are not limited to, EDTA, glycine and citric acid or salts thereof.

In another embodiment, the antioxidant reducing agent useful in this invention include, but are not limited to sulfite, bisulfite, metabisulfite, butylatedhydroxytoluene (BHT), butylatedhydroxyanisole (BHT) or a mixture thereof. A reducing agent inhibits oxidation reaction of the drug, oil or phospholipid components and prevents discoloration of the emulsions.

In certain embodiments, the concentration of antioxidant in the emulsion is from about 0.0001% to about 1% w/v. In certain embodiments, the concentration of antioxidant in the emulsion is from about 0.001% to about 0.1% w/v. In still further embodiments, the concentration of the antioxidant in the emulsion is from about 0.001% to about 0.005% w/v.

In certain embodiments, the concentration of EDTA in the emulsion can be from about 0.0001% to about 0.01% w/v.

In certain embodiments the antioxidant reducing agent useful in this invention include, but are not limited to, the sulfite, bisulfite, or metabisulfite is a sodium or potassium salt.

In certain embodiments, the concentration of sulfite, bisulfite, or metabisulfite is from about 0.001% to about 0.2% w/v. In some embodiments, the concentration of sulfite, bisulfite, or metabisulfite is from about 0.01% to about 0.1% w/v.

In certain embodiments, the concentration of butylatedhydroxytoluene (BHT), butylatedhydroxyanisole (BHT) is from about 0.0001% to about 0.002% w/v.

As used herein, the term "preservatives" refers to agents that can prevent microbial growth in the emulsion formulation of this invention. The oil-in-water emulsions of the present application may be conducive for microbial growth or contamination. Therefore, a preservative may be desirable in the composition, especially for a vialed product that is intended to provide multiple doses where multiple punctures of the vial stopper by syringe needles are needed. The preservatives useful for this invention include, but are not limited to, sodium edetate (EDTA), sodium metabisulfite, sodium benzoate, benzyl alcohol, bronopol, parabens, cresol, phenol, phenoxyethanol, phenylmercuric acetate, phenylmercuric borate, phenylmercuric nitrate, sorbate, benzoate, sorbic acid thimerosal, cetrimide, chlorhexidine, chlorobutanol, chlorocresol, benzalkonium chloride and benzethonium chloride or a mixture thereof The aqueous (water) phase of an oil-in-water emulsion of the present composition is usually at a concentration of at least about 70% by weight of the emulsion composition. In certain embodiments, the aqueous phase is at a concentration of about 70% to about 95% by weight of the emulsion. In some embodiments, the aqueous phase is at a concentration of about 75%. In some embodiments, the aqueous phase is at a concentration of about 80%. In some embodiments, the aqueous phase is at a concentration of about 85%. In some embodiments, the aqueous phase is at a concentration of about 90%. In some embodiments, the aqueous phase is at a concentration of about 95%.

In one embodiment, the present application provides a parenteral composition of diclofenac or its pharmaceutically acceptable salt, wherein the composition provides $AUC_{(0-inf)}$ from about 900 ng/mL*h to about 5000 ng/mL*h. In some embodiments, the present application provides a parenteral composition of diclofenac or its pharmaceutically acceptable salt, wherein the composition provides $AUC_{(0-inf)}$ from about 1000 ng/mL*h to about 2000 ng/mL*h. In some embodiments, the present application provides a parenteral composition of diclofenac or its pharmaceutically acceptable salt, wherein the composition provides $AUC_{(0-inf)}$ such as 900 ng/mL*h, 1000 ng/mL*h, 1200 ng/mL*h, 1400 ng/mL*h, 1600 ng/mL*h, 1800 ng/mL*h, 2000 ng/mL*h. In one embodiment, the present application provides a parenteral composition of diclofenac or its pharmaceutically acceptable salt, wherein the composition provides $AUC_{(0-t)}$ from about 900 ng/mL*h to about 5000 ng/mL*h. In some embodiments, the present application provides a parenteral composition of diclofenac or its pharmaceutically acceptable salt, wherein the composition provides $AUC_{(0-t)}$ from about 1000 ng/mL*h to about 2000 ng/mL*h. In some embodiments, the present application provides a parenteral composition of diclofenac or its pharmaceutically acceptable salt, wherein the composition provides $AUC_{(0-t)}$ such as 900 ng/mL*h, 1000 ng/mL*h, 1200 ng/mL*h, 1400 ng/mL*h, 1600 ng/mL*h, 1800 ng/mL*h, 2000 ng/mL*h.

In one embodiment, the present application provides parenteral composition of 18.75 mg of diclofenac sodium, comprising
 (a) an oil component,
 (b) a phospholipid component, and
 (c) water
wherein the composition has 90% Confidence Interval of the relative mean $AUC_{(0-inf)}$ upon the administration to humans is within 80.00% to 125.00% of $AUC_{(0-inf)}$ of CATAFLAM® 50 mg oral tablets, when administered in the fasting state.

In one embodiment, the present application provides parenteral composition of 18.75 mg of diclofenac sodium, comprising
(a) an oil component,
(b) a phospholipid component, and
(c) water
wherein the composition has 90% Confidence Interval of the relative mean $AUC_{(0-t)}$ upon the administration to humans is within 80.00% to 125.00% of $AUC_{(0-t)}$ of CATAFLAM® 50 mg oral tablets, when administered in the fasting state.

In one embodiment, the present application provides a parenteral composition of diclofenac or its pharmaceutically acceptable salt, wherein the composition provides $C_{max}$ or $C_0$ (ng/ml) from about 3000 ng/ml to about 14000 ng/ml. In another embodiment, the present application provides a parenteral composition of diclofenac or its pharmaceutically acceptable salt, wherein the composition provides $C_{max}$ or $C_0$ (ng/ml) from about 4000 ng/ml to about 12000 ng/ml. Coefficients of variation (CV %) as a means of determining inter-subject variability in absorption as determined in conventional manner as a percentage, e.g. on the basis of the standard deviation in the mean AUC in ng/mL*h divided by the mean AUC in ng/mL*h. The higher the coefficients of variation higher the variations in AUC observed and inconsistent efficacy of the composition and vice-versa. CATAFLAM® provides $AUC_{(0-t)}$ with a coefficient of variation of about 30% and $AUC_{(0-inf)}$ with a coefficient of variation of about 30%.

The term "$C_{max}$" as used herein, refers to the maximum plasma concentration of diclofenac or its pharmaceutically acceptable salt, after oral administration.

The term "$C_0$" as used herein, refers to the initial plasma concentration of diclofenac or its pharmaceutically acceptable salt, after intravenous bolus administration (measured within 2±1 minute after administration).

In one embodiment, the present application provides a parenteral composition of diclofenac or its pharmaceutically acceptable salt, wherein the composition provides $AUC_{(0-t)}$ of at least about 900 ng/mL*h with a coefficient of variance (CV %) of less than about 30%. In some embodiments, the present application provides a parenteral composition of diclofenac or its pharmaceutically acceptable salt, wherein the composition provides $AUC_{(0-t)}$ of at least about 900 ng/mL*h with a coefficient of variance (CV %) of less than 25%. In some embodiments, the present application provides a parenteral composition of diclofenac or its pharmaceutically acceptable salt, wherein the composition provides $AUC_{(0-t)}$ of at least about 900 ng/mL*h with a coefficient of variance (CV %) of less than about 20%. In some embodiments, the present application provides a parenteral composition of diclofenac or its pharmaceutically acceptable salt, wherein the composition provides $AUC_{(0-t)}$ of at least about 900 ng/mL*h with a coefficient of variance (CV %) of less than about 15%.

In one embodiment, the present application provides a parenteral composition of diclofenac or its pharmaceutically acceptable salt, wherein the composition provides $AUC_{(0-inf)}$ with a coefficient of variance (CV %) of less than about 30%. In some embodiments, the present application provides a parenteral composition of diclofenac or its pharmaceutically acceptable salt, wherein the composition provides $AUC_{(0-inf)}$ with a coefficient of variance (CV %) of less than about 25%. In some embodiments, the present application provides a parenteral composition of diclofenac or its pharmaceutically acceptable salt, wherein the composition provides $AUC_{(0-inf)}$ with a coefficient of variance (CV %) of less than about 20%. In some embodiments, the present application provides a parenteral composition of diclofenac or its pharmaceutically acceptable salt, wherein the composition provides $AUC_{(0-inf)}$ with a coefficient of variance (CV %) of less than about 15%.

In certain embodiments, the components of the oil-in-water emulsion (e.g., the drug, an oil component, a phospholipid component, a stabilizer, and a tonicity modifier) are safe, well tolerated, and acceptable by the FDA for intravenous/intramuscular injection.

A component of oil-in-water emulsions is regarded as "safe" if it does not cause undesired systemic or local reactions (e.g., anaphylactic shock) in patients. A component of oil-in-water emulsions is regarded as "well tolerated" if it does not result in substantially adverse effects at the injection site, such as phlebitis, vein inflammation or vein irritation.

In certain embodiments, the oil-in-water emulsions of the present composition are vein non-irritating. "Vein non-irritating" refers to the property of a compound or composition, when administered intravenously, does not cause substantial irritation at the injection site, as evident by, for example, thickened skin, necrotic skin, local redness, local swelling, venous dilation with blood clot formation, or venous embolism with subcutaneous inflammation.

In certain embodiments, the present compositions are both chemically and physically stable. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 6 months. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 12 months. In some embodiments, the composition is "chemically stable" if the diclofenac or its pharmaceutically acceptable salt in the composition is maintained at a concentration of no less than 90% of the initial concentration of diclofenac when stored at a temperature of about 2-8° C. or about 25° C. for a period to about 24 months.

In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 1 month. In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 6 months. In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 12 months. In some embodiments, a nanoemulsion is "physically stable" if it remains precipitate-free, and maintains a mean oil droplet diameter less than 200 nm and a PFAT5 less than 0.05% when stored at a temperature of about 2-8° C. or about 25° C. for about 24 months.

In still another aspect, the composition of the present application relates to emulsions that are ready-to-use for intravenous injection/infusion/intramuscular injection. The term "ready to use" means that the pharmaceutical compositions can be used as is or without a need for further dilution, mixing, or other alteration of its composition prior to use.

In certain embodiments, the present emulsions may be parenterally administered to a subject. "Parenteral" includes any mode of administration that does not go through the digestive tract, but excludes trans-membrane delivery such as skin patches.

In certain embodiments, the mode of administration of the present emulsions is by intravenous, intra-arterial, intrathecal, intraperitoneal, intraocular, intra-articular, intramuscular or subcutaneous injection.

Besides being ready-to-use oil-in-water emulsions, the compositions of the present application can also be prepared with a cryoprotectant(s) as a lyophilized solid, i.e., "an oil-in-solid dispersion system" that can be reconstituted at a later date and diluted with water to reform the oil-in-water emulsion before injection. It can also be diluted with, but are not limited to, saline, dextrose injections.

As used herein, the term "an oil-in-solid dispersion system" refers to a solid matrix prepared by freeze-drying (lyophilizing) an oil-in-water emulsion, which can reform an oil-in-water emulsion of similar droplet size upon mixing with water (reconstitution). In certain embodiments, the average droplet size of the reformed emulsion is no more than about 500%, of the average droplet size of the emulsion before the freeze-drying. In some embodiments, the average droplet size of the reformed emulsion is no more than about 400% of the average droplet size of the emulsion before the freeze-drying. In some embodiments, the average droplet size of the reformed emulsion is no more than about 300% of the average droplet size of the emulsion before the freeze-drying. In some embodiments, the average droplet size of the reformed emulsion is no more than about 200% of the average droplet size of the emulsion before the freeze-drying. In some embodiments, the average droplet size of the reformed emulsion is no more than about 150% of the average droplet size of the emulsion before the freeze-drying. An oil-in-solid dispersion system of this invention may be optionally prepared by spray drying.

"Cryoprotectants" refers to those ingredients which are added to maintain the discrete and submicron droplets of the emulsion during the freeze-drying process and, upon the removal of water of the emulsion, to provide a solid matrix for the droplets to form the oil-in-solid dispersion system. Exemplary cryoprotectants include, but not limited to, polyols, monosaccharides, disaccharides, polysaccharides, amino acids, peptides, proteins, and hydrophilic polymers, or mixtures thereof. Examples of polyols include glycerin, mannitol, erythritol, maltitol, xylitol, sorbitol, polyglycitol or mixtures thereof. Examples of monosaccharides include glucose, mannose, fructose, lactulose, allose, altrose, gulose, idose, galactose, talose, ribose, arabinose, xylose, lyxose or mixtures thereof. Examples of disaccharides include sucrose, lactose, maltose, isomaltose, trehalose, cellubiose or mixtures thereof. Examples of polysaccharides include cellulose, amylase, inulin, chitin, chitosan, amylopectin, glycogen, pectin, hyaruronic acid or mixtures thereof. Examples of amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or mixtures thereof. Examples of peptides include diglycine and triglycine. Examples of proteins include albumin, collagen, casein, and gelatin. Examples of hydrophilic polymers include, but are not limited to, polyethylene glycols, povidones, poloxamers, polyvinyl alcohols or mixtures thereof.

In certain embodiments, the concentration of a cryoprotectant sufficient for stabilizing the oil droplets of an emulsion and is present in the range of about 2% to about 40% w/w. In some embodiments, the concentration of the cryoprotectant is present in the range of about 5% to about 25% w/w. In further embodiments, the concentration of the cryoprotectant is present in the range of and about 10% to about 20% w/w.

In one aspect the present application also provides methods for preparing parenteral composition in the form of oil-in-water emulsions for delivering diclofenac or its pharmaceutically acceptable salt as described herein.

In one embodiment, the emulsion may be prepared by the process comprising the steps of:
  (a) forming a mixture that comprises appropriate amounts of
    (i) diclofenac or its pharmaceutically acceptable salt,
    (ii) an oil component (e.g., a vegetable oil, or a combination of a vegetable oil and a medium chain triglyceride), and
    (iii) a phospholipid component, and
  (b) forming an oil-in-water emulsion with the mixture of step (a) and an aqueous solution.

In certain embodiments, step (b) may be performed by adding the aqueous solution to the mixture of step (a) to form a primary emulsion. In some embodiments, the aqueous solution is a water or a buffer solution, and may contain stabilizer(s) and/or tonicity modifier(s). In some embodiments, the formation of the primary emulsion may be performed or facilitated by the use of mechanical homogenization (e.g., high shear mixing, high pressure extrusion, and microfluidization) or other suitable techniques.

In some embodiments, the methods may further comprise one or more of the following steps: (A) combining all components in any order of addition, (B) mixing and homogenizing to dissolve diclofenac or its pharmaceutically acceptable salt and to provide an emulsion with a mean droplet diameter less than about 200 nm, and (C) sterilizing the emulsion by filtration using a 0.2 μm filter.

In certain embodiments, the composition of present application may be sterilized by autoclave methods.

In some embodiments, the methods may further comprise one or more steps to adjust the pH of the emulsion to a desirable range, and such adjustment can take place at any step before or after the sterilization step.

In one embodiment, the composition of present application provides methods of treating pain associated with spinal cord injuries, traumatic brain injuries, strokes, injuries to the peripheral nerves system, injuries to the central nerves systems or injuries to other systems having nerve tissue, preferably the injury has associated with it inflammation, where the methods include the step of administering a composition of this invention to an mammal including a human or directly to the site of injury or into the blood or other bodily fluid of the mammal including a human.

In one embodiment, the composition of present application provides methods of treating pain associated with field injuries such as combat injuries or accident injuries, where the methods include the steps of administering an amount of a composition of this invention directly to the injury or to the surrounding tissue to reduce inflammation while preventing ulceration of the injury or while maintaining the integrity of hydrophobic membranes and/or layers that may be associated with the injured site, where the amount of the composition administered is sufficient to cause a desired pharmacological effect.

In certain embodiments, the compositions of present application are used in pain management. The composition can be used in postoperative pain management, battle field pain management, accident pain management, or other pain management under emergency conditions without the significant side effects of alternative pain management medications such as opiates.

In some embodiments, compositions of the present application can be used for the treatment of migraine pain with or without aura.

In one embodiment, composition of present application is ready-to-use because it is about isotonic, pH neutral and non-vein irritating, and can be injected without any further adjustment, dilution or mixing with other liquid.

In another embodiment, composition of present application can be diluted with another injectable solution such as normal saline, dextrose solution, ringer's lactate solution or other compatible injectable drug solution prior to injection.

In another embodiment, composition of present application can be administered parenterally such as intravenous bolus injection, intravenous infusion, intra-arterial, intrathecal, intraperitoneal, intraocular, intra-articular, intramuscular or subcutaneous injection.

In another embodiment, the present application also provides an injection apparatus including a reservoir including a volume of a composition of this invention sufficient to cause a desired pharmacological effect, a plunger operably connected to the reservoir and a needle operably connected to an other end of the reservoir, where the volume is injected through the needle when the plunger is depressed.

In one embodiment, the present application also provides a kit for emergency administration of a sterile injectable pain relieving diclofenac compositions, where the kit includes an injector apparatus including a manual or electrically powered syringe, a needleless injection system or other apparatus that can inject the composition into a body of a mammal including a human. The kit also includes containers including doses of at least one diclofenac composition sufficient to cause desired pharmacologic effects.

The present invention is illustrated below by reference to the following examples. However, one skilled in the art will appreciate that the specific methods and results discussed are merely illustrative of the invention, and not to be construed as limiting the invention.

EXAMPLES

Examples 1-6

| Composition | Example 1 (%) | Example 2 (%) | Example 3 (%) | Example 4 (%) | Example 5 (%) | Example 6 (%) |
|---|---|---|---|---|---|---|
| Diclofenac sodium | 3.75 | 3.75 | 3.75 | 3.75 | 3.75 | 3.75 |
| Medium chain triglycerides (MIGLYOL 812) | 0 | 2.5 | 5 | 0 | 0 | 0 |
| Soybean oil, super refined | 5 | 2.5 | 0 | 5 | 5 | 5 |
| Egg lecithin (LIPOID E-80) | 10 | 10 | 10 | 15 | 0 | 0 |
| Soy lecithin (LIPOID S-100) | 0 | 0 | 0 | 0 | 10 | 15 |
| EDTA disodium dehydrate USP | 0.0055 | 0.0055 | 0.0055 | 0.0055 | 0.0055 | 0.0055 |
| Purified water | q.s. | q.s. | q.s. | q.s. | q.s. | q.s. |
| pH | 7.4 | 7.65 | 7.52 | 7.47 | 7.83 | 7.82 |

Procedure:
i. All the components are weighed in a clean beaker and mixed well in high shear mixer.
ii. The mixture of step i. is subjected to microfluidization homogenization.
iii. The pH of the mixture step ii. is adjusted to the required pH.
iv. The mixture of step iii. is passed through 0.22µ filter.

Examples 7-10

| Composition | Example 7 (%) | Example 8 (%) | Example 9 (%) | Example 10 (%) |
|---|---|---|---|---|
| Diclofenac sodium | 3.75 | 3.75 | 3.75 | 3.75 |
| Medium chain triglycerides (MIGLYOL 812) | 5 | 5 | 5 | 5 |
| Egg lecithin (LIPOID E-80) | 10 | 10 | 10 | 10 |
| EDTA disodium dehydrate USP | 0.0055 | 0.0055 | 0.0055 | 0.0055 |
| Sucrose, USP/NF | 15 | 15 | 15 | 15 |
| Purified water | q.s. | q.s. | q.s. | q.s. |
| pH | 7.5 | 8.5 | 8.0 | 7.0 |

Procedure:
The compositions are prepared as per the procedure mentioned in Examples 1-6.

Examples 11-15

| Composition | Example 11 (%) | Example 12 (%) | Example 13 (%) | Example 14 (%) | Example 15 (%) |
|---|---|---|---|---|---|
| Diclofenac sodium | 3.75 | 3.75 | 3.75 | 3.75 | 3.75 |
| Medium chain triglycerides (MIGLYOL 812) | 5 | 5 | 5 | 5 | 5 |
| Egg lecithin (LIPOID E-80) | 10 | 10 | 10 | 10 | 10 |
| EDTA disodium dehydrate USP | 0.0055 | 0.0055 | 0.0055 | 0.0055 | 0.0055 |
| Sucrose, USP/NF | 10 | 5 | 10 | 5 | 6 |
| Purified water | q.s. | q.s. | q.s. | q.s. | q.s. |
| pH | 7.5 | 7.5 | 8.1 | 7.9 | 7.9 |

Procedure:
The compositions are prepared as per the procedure mentioned in Examples 1-6.

Examples 16-20

| Composition | Example 16 (%) | Example 17 (%) | Example 18 (%) | Example 19 (%) | Example 20 (%) |
|---|---|---|---|---|---|
| Diclofenac sodium | 3.75 | 3.75 | 3.75 | 3.75 | 3.75 |
| Medium chain triglycerides (MIGLYOL 812) | 5 | 5 | 5 | 5 | 5 |
| Egg lecithin (LIPOID E-80) | 10 | 10 | 10 | 10 | 10 |
| EDTA disodium dehydrate USP | 0.0055 | 0.0055 | 0.0055 | 0.0055 | 0.0055 |
| Sucrose, USP/NF | 7 | 8 | 8 | 10 | 8 |
| Purified water | q.s. | q.s. | q.s. | q.s. | q.s. |
| pH | 7.9 | 7.9 | 7.9 | 7.9 | 8.0 |

Procedure:
The compositions are prepared as per the procedure mentioned in Examples 1-6.

Examples 21-25

| Composition | Example 21 (%) | Example 22 (%) | Example 23 (%) | Example 24 (%) | Example 25 (%) |
|---|---|---|---|---|---|
| Diclofenac sodium | 3.75 | 3.75 | 3.75 | 3.75 | 3.75 |
| Medium chain triglycerides (MIGLYOL 812) | 5 | 5 | 4 | 3 | 2 |
| Egg lecithin (LIPOID E-80) | 10 | 10 | 10 | 10 | 10 |
| Sodium oleate | 0 | 0.03 | 0 | 0 | 0 |
| EDTA disodium dehydrate USP | 0.0055 | 0.0055 | 0.0055 | 0.0055 | 0.0055 |
| Sucrose, USP/NF | 5 | 8 | 8 | 8 | 8 |
| Purified water | q.s. | q.s. | q.s. | q.s. | q.s. |
| pH | 8.0 | 8.0 | 8.0 | 8.0 | 8.0 |

Procedure:

The compositions are prepared as per the procedure mentioned in Examples 1-6.

Examples 26-29

| Composition | Example 26 (%) | Example 27 (%) | Example 28 (%) | Example 29 (%) |
|---|---|---|---|---|
| Diclofenac sodium | 3.75 | 3.75 | 3.75 | 3.75 |
| Medium chain triglycerides (MIGLYOL 812) | 1 | 7.5 | 2.5 | 1 |
| Egg lecithin (LIPOID E-80) | 10 | 7.5 | 12.5 | 14 |
| Sodium oleate | 0 | 0.03 | 0 | 0 |
| EDTA disodium dehydrate USP | 0.0055 | 0.0055 | 0.0055 | 0.0055 |
| Sucrose, USP/NF | 8 | 8 | 8 | 8 |
| Purified water | q.s. | q.s. | q.s. | q.s. |
| pH | 8.0 | 8.0 | 8.0 | 8.0 |

Procedure:

The compositions are prepared as per the procedure mentioned in Examples 1-6.

Example 30

Bioavailability Studies

A randomized, parallel-group, single-center study in healthy subjects to assess the safety and pharmacokinetics of diclofenac nanoemulsion of Example 21 (having diclofenac sodium of 18.75 mg and 37.5 mg) in comparison with oral diclofenac potassium tablets (CATAFLAM® 50 mg).

Study Objective:

The objective of this study was to characterize the PK profile of single and multiple bolus doses of diclofenac nanoemulsion as compared with the PK profile of oral Cataflam®.

Study Design:

All subjects received 1 oral Cataflam® 50-mg diclofenac tablet under fasted conditions on Day 1 and underwent a washout period on Days 2 through 4. Subjects were randomized equally to receive 1 of 3 treatments (A, B, or C) once under fasted conditions on Day 5, q6 hours from Day 6 until (but not including) the last dose of the study on the morning of Day 12 (beginning 24 hours after the Day 5 dose), and under fasted conditions on the morning of Day 12 (last dose of the study):

Treatment A: Placebo matching composition of Example 21.

Treatment B: Example 21 with diclofenac sodium 18.75 mg in 0.5 mL (Test)

Treatment C: Example 21 with diclofenac sodium 37.5 mg in 1 mL (Test)

The site of IV drug administration was used solely for that purpose. Pharmacokinetic samples were not obtained from the drug administration site. Pharmacokinetic samples collected over the first hour after dosing were collected from the arm opposite to the arm used for the IV bolus administration.

Study Results:

A) Pharmacokinetic Assessments:

Blood samples for determination of diclofenac plasma concentrations were collected at specified time points on Days 1, 5, and 12. On Day 1, blood samples were collected at specified time points relative to dosing with Cataflam® 50 mg. On Day 5, blood samples were collected at specified time points relative to the IV bolus dose of the study drug administered (Treatments A, B, or C). On Day 12, blood samples were collected at specified time points relative to the morning dosing (last dose) on Day 12. Blood samples for PK analysis were collected at the predose time point (Time 0); 2, 5, 10, 15, and 20 minutes after dosing; and 0.5, 0.75, 1, 1.5, 2, 3, 4, 6, 8, 10, 12, and 24 hours after dosing. The predose sample was obtained within 30 minutes before dosing. Postdose PK blood samples collected at time points 0.5 hours after dosing were obtained within ±1 minute of the scheduled sampling time. Postdose PK blood samples collected at time points >0.5 hours to <24 hours after dosing were obtained within ±2 minutes of the scheduled sampling time. The PK blood sample collected at 24 hours after dosing was obtained within ±5 minutes of the scheduled sampling time.

TABLE 1

Summary of Key Pharmacokinetic Parameters (Pharmacokinetic Population)

| | | Single Dosing | | Multiple Dosing | |
|---|---|---|---|---|---|
| Parameter Statistic | Cataflam® 50 mg Oral (n = 42) | Example 21 18.75 mg IV Bolus (n = 14) | Example 21 37.5 mg IV Bolus (n = 14) | Example 21 18.75 mg IV Bolus (n = 14) | Example 21 37.5 mg IV Bolus (n = 14) |
| $AUC_{0-t}$ (ng/mL * h) | | | | | |
| Mean | 1297.5 | 1225.0 | 2573.4 | 1150.0 | 2338.2 |
| SD | 391.59 | 148.27 | 426.45 | 181.29 | 305.69 |
| Median | 1370 | 1175 | 2465 | 1170 | 2339 |
| % CV | 30.2 | 12.1 | 16.6 | 15.8 | 13.1 |
| $AUC_{0-inf}$ (ng/mL * h) | | | | | |
| Mean | 1308.9 | 1232.4 | 2582.2 | | |
| SD | 393.04 | 147.59 | 426.64 | | |
| Median | 1381 | 1182 | 2474 | | |
| % CV | 30.0 | 12.0 | 16.5 | | |

TABLE 1-continued

Summary of Key Pharmacokinetic Parameters (Pharmacokinetic Population)

| Parameter Statistic | Cataflam ® 50 mg Oral (n = 42) | Single Dosing | | Multiple Dosing | |
|---|---|---|---|---|---|
| | | Example 21 18.75 mg IV Bolus (n = 14) | Example 21 37.5 mg IV Bolus (n = 14) | Example 21 18.75 mg IV Bolus (n = 14) | Example 21 37.5 mg IV Bolus (n = 14) |
| $C_{max}$ or $C_0$ (ng/mL)$^a$ | | | | | |
| Mean | 1041.4 | 6143.6 | 11702.0 | 6024.8 | 10914.9 |
| SD | 607.37 | 2503.45 | 5029.76 | 3014.28 | 4506.84 |
| Median | 1000 | 6343 | 11100 | 6345 | 10923 |
| % CV | 58.3 | 40.7 | 43.0 | 50.0 | 41.3 |
| $t_{1/2}$ (h) | | | | | |
| Mean | 2.09 | 1.26 | 1.78 | 1.70 | 2.45 |
| SD | 0.752 | 0.240 | 0.374 | 0.313 | 0.854 |
| Median | 2.0 | 1.2 | 1.7 | 1.7 | 2.4 |
| % CV | 35.9 | 19.1 | 21.0 | 18.4 | 34.9 |

% CV = coefficient of variation %;
$AUC_{0-t}$ = area under the concentration-time curve from Time 0 to the time of last sample with a quantifiable concentration;
$AUC_{0-tau}$ = area under the concentration-time curve from time 0 to the end of the treatment period.
Tau = 6 hours;
$AUC_{0-inf}$ = area under the concentration time curve from time 0 to the last quantifiable concentration then extrapolated to infinity;
$C_0$ = initial plasma concentration;
SD = standard deviation;
$t_{1/2}$ = terminal half-life;
$T_{max}$ = time to maximum concentration;

B) Single-Dose Bioavailability Comparison to Cataflam® 50 mg.

The single-dose bioavailability comparison between the 2 strengths of IV bolus diclofenac nanoemulsion (18.75 and 37.5 mg) and oral Calaflam® (50 mg) were made using the $AUC_{0-t}$ and the $AUC0_{-inf}$ measures of extent of availability. Both strengths of IV bolus of diclofenac composition had greater bioavailability than oral Calaflam. Results of the comparisons were similar because the measures of AUC were similar.

The 18.75-mg IV bolus of diclofenac composition had an $AUC_{0-t}$ ratio point estimate of 107.5%, with a 90% confidence interval (CI) of 95.8 to 120.7%. For the $AUC_{0-inf}$ ratio comparisons, the 18.75-mg IV bolus of diclofenac nanoemulsion had a ratio point estimate of 107.1%, with a 90% CI of 95.5 to 120.2%.

The 37.5-mg bolus had an $AUC_{(0-t)}$ ratio point estimate of 187.3%, with a 90% CI of 167.6 to 209.4%.

For $AUC_{(0-inf)}$ the 37.5-mg bolus had a ratio point estimate of 186.5%, with a 90% CI of 166.9 to 208.4%.

Example 31

Safety Assessment of IV Bolus Diclofenac Composition (18.75 and 37.5 mg)

Safety was assessed of both strengths (18.75 and 37.5 mg) in 28 subjects primarily on the basis of local tolerance (venous irritation, phlebitis, and/or thrombophlebitis), with recording of the grade of the Thrombophlebitis Assessment (scale of 0-5).

Thrombophlebitis assessment was performed for each subject predose (after the IV catheter was placed and before each bolus was administered), immediately after each IV dose, q6 hours after the initial IV dose administered on Day 5 and continuing through Day 12, immediately before and after each change or discontinuation of IV access site during the inpatient phase, on Day 13, and at the follow-up visit.

Thrombophlebitis Assessment

| Grade | Description |
|---|---|
| 0 | No reaction |
| 1 | Tenderness along the vein |
| 2 | Continuous tenderness or pain with redness |
| 3 | Palpable swelling or thrombosis within length of the cannula |
| 4 | Palpable swelling or thrombosis beyond the length of the cannula |
| 5 | As for Grade 4, with overt infection |

Results:

After a single IV dose of the diclofenac nanoemulsion, 3 subjects (2 subjects [14.3%] in the placebo group and 1 subject [7.1%] in the diclofenac 18.75-mg group) reported Grade 1 thrombophlebitis. No subjects in any group reported higher than Grade 1 thrombophlebitis after receiving a single IV dose.

The incidence of Grade 1 thrombophlebitis after the multiple-dose phase ranged from 28.6% (diclofenac 18.75 mg and diclofenac 37.5 mg) to 35.7% (placebo). Of the 9 subjects who reported Grade 2 or higher thrombophlebitis, 2 subjects (14.3%) each were in the placebo and diclofenac 37.5 mg groups and 5 (35.7%) were in the diclofenac 18.75-mg group.

Example 32

To further define some useful weight % limits for the phospholipids, oil, and the aqueous phase, a phase diagram study was conducted by preparing and testing formulations in varying concentrations of phospholipid component, oil component and aqueous phase in the following compositions:

TABLE 2

| Composition (% wt) | Ex. 32-1 | Ex. 32-2 | Ex. 32-3 | Ex. 32-4 | Ex. 32-5 | Ex. 32-6 | Ex. 32-7 (F)* | Ex. 32-8 | Ex. 32-9 | Ex. 32-10 | Ex. 32-11 | Ex. 32-12 | Ex. 32-13 | Ex. 32-14 |
|---|---|---|---|---|---|---|---|---|---|---|---|---|---|---|
| Diclofenac sodium | 3.75 | 3.75 | 3.75 | 3.75 | 3.75 | 3.75 | 3.75 | 3.75 | 3.75 | 3.75 | 3.75 | 3.75 | 3.75 | 3.75 |
| Medium chain triglyceride | 0 | 4 | 0 | 0 | 2 | 0 | 10 | 15 | 14 | 13.5 | 12 | 10.5 | 9 | 7.5 |
| Lecithin | 1 | 1 | 5 | 8 | 8 | 10 | 1.2 | 0 | 1 | 1.5 | 3 | 4.5 | 6 | 7.5 |
| EDTA disodium dehydrate | 0.0055 | 0.0055 | 0.0055 | 0.0055 | 0.0055 | 0.0055 | 0.0055 | 0.0055 | 0.0055 | 0.0055 | 0.0055 | 0.0055 | 0.0055 | 0.0055 |
| Sucrose | 5 | 5 | 5 | 5 | 5 | 5 | 5 | 5 | 5 | 5 | 5 | 5 | 5 | 5 |
| Purified water | q.s. | q.s. | q.s. | q.s. | q.s. | q.s. | q.s. | q.s. | q.s. | q.s. | q.s. | q.s. | q.s. | q.s. |

TABLE 3

| Composition (% wt) | Ex. 32-15 (=Ex. 21) | Ex. 32-16 | Ex. 32-17 | Ex. 32-18 | Ex. 32-19 | Ex. 32-20 | Ex. 32-21 | Ex. 32-22 | Ex. 32-22 | Ex. 32-24 | Ex. 32-25 | Ex. 32-26 | Ex. 32-27 | Ex. 32-28 |
|---|---|---|---|---|---|---|---|---|---|---|---|---|---|---|
| Diclofenac sodium | 3.75 | 3.75 | 3.75 | 3.75 | 3.75 | 3.75 | 3.75 | 3.75 | 3.75 | 3.75 | 3.75 | 3.75 | 3.75 | 3.75 |
| Medium chain triglyceride | 0 | 4 | 0 | 0 | 2 | 0 | 10 | 15 | 14 | 13.5 | 12 | 10.5 | 9 | 7.5 |
| Lecithin | 1 | 1 | 5 | 8 | 8 | 10 | 1.2 | 0 | 1 | 1.5 | 3 | 4.5 | 6 | 7.5 |
| EDTA disodium dehydrate | 0.0055 | 0.0055 | 0.0055 | 0.0055 | 0.0055 | 0.0055 | 0.0055 | 0.0055 | 0.0055 | 0.0055 | 0.0055 | 0.0055 | 0.0055 | 0.0055 |
| Sucrose | 5 | 5 | 5 | 5 | 5 | 5 | 5 | 5 | 5 | 5 | 5 | 5 | 5 | 5 |
| Purified water | q.s. | q.s. | q.s. | q.s. | q.s. | q.s. | q.s. | q.s. | q.s. | q.s. | q.s. | q.s. | q.s. | q.s. |

* Same composition as in DIPRIVAN ® (Propofol injectable Emulsion, USP)

All formulations were prepared as per the procedure used in Examples 1-6 and according to the table 2 and 3. Each composition was checked for precipitates of diclofenac sodium and physical stability (viscosity and clarity). An acceptable composition was defined as a "nanoemulsion" and was selected based on absence of precipitation of diclofenac sodium and acceptable appearance and droplet size after storage at 2-8° C. for 3 days.

A ternary phase diagram was drawn (FIG. 1) which depicts the "nanoemulsion region" (grey area). The "nanoemulsion region" is defined by connecting lines between five critical compositions (A, B, C, D and E). Any composition that is outside of this region does not form an acceptable nanoemulsion because it is either incapable of solubilizing diclofenac sodium, too viscous to process or not having the droplet size less than 200 nm. For example, a composition (F) which has the same phospholipids and oil contents as in the Propofol Injectable Emulsion is outside the "nanoemulsion" region and has failed to solubilize diclofenac sodium.

TABLE 4

| ID | Phospholipids (% wt) | Oil (% wt) | Aqueous Phase (% wt) | Precipitation | Locator ID in the Phase Diagram (FIG. 1) |
|---|---|---|---|---|---|
| Example 32-1 | 1 | 0 | 95.25 | Yes | Open circle |
| Example 32-2 | 1 | 4 | 91.25 | Yes | Open circle |
| Example 32-3 | 5 | 0 | 91.25 | Yes | Open circle |
| Example 32-4 | 8 | 0 | 88.25 | Yes | Open circle |
| Example 32-5 | 8 | 2 | 86.25 | No | B, Solid circle |
| Example 32-6 | 10 | 0 | 86.25 | No | A, Solid circle |
| Example 32-7 (F)* | 1.2 | 10 | 85.05 | Yes | F, Open circle |
| Example 32-8 | 0 | 15 | 81.25 | Yes | Open circle |
| Example 32-9 | 1 | 14 | 81.25 | Yes | Open circle |

TABLE 4-continued

| ID | Phospholipids (% wt) | Oil (% wt) | Aqueous Phase (% wt) | Precipitation | Locator ID in the Phase Diagram (FIG. 1) |
|---|---|---|---|---|---|
| Example 32-10 | 1.5 | 13.5 | 81.25 | Yes | Open circle |
| Example 32-11 | 3 | 12 | 81.25 | Yes | Open circle |
| Example 32-12 | 4.5 | 10.5 | 81.25 | Yes | Open circle |
| Example 32-13 | 6 | 9 | 81.25 | Yes | Open circle |
| Example 32-14 | 7.5 | 7.5 | 81.25 | No | Solid circle |
| Example 32-15 | 10 | 5 | 81.25 | No | Solid circle |
| Example 32-16 | 12 | 3 | 81.25 | No | Solid circle |
| Example 32-17 | 15 | 0 | 81.25 | No | Solid circle |
| Example 32-18 | 4 | 16 | 76.25 | Yes | Open circle |
| Example 32-19 | 5 | 15 | 76.25 | Yes | Open circle |
| Example 32-20 | 6 | 14 | 76.25 | No | Solid circle |
| Example 32-21 | 8 | 12 | 76.25 | No | Solid circle |
| Example 32-22 | 20 | 0 | 76.25 | No | E, Solid circle |
| Example 32-23 | 4 | 21 | 71.25 | Yes | Open circle |
| Example 32-24 | 5 | 20 | 71.25 | No | Solid circle |
| Example 32-25 | 6 | 19 | 71.25 | No | Solid circle |
| Example 32-26 | 8 | 17 | 71.25 | No | Solid circle |
| Example 32-27 | 4 | 26 | 66.25 | No | Open square |
| Example 32-28 | 3 | 32 | 61.25 | No | C, Open square |
| Example 32-29 | 18 | 17 | 61.25 | No | D, Open square |

**Same composition as in DIPRIVAN ® (Propofol Injectable Emulsion, USP)

FIG. 1: Phase diagram depicting a "nanoemulsion region" (grey area), which is defined by connecting lines between five compositions (A, B, C, D and E). Any composition that is outside of this region does not form an acceptable nanoemulsion because it is either incapable of solubilizing diclofenac sodium, too viscous to process or not having the droplet size less than 200 nm. For example, a composition (Example 32-7F) which has the same phospholipids and oil contents as in the Propofol Injectable Emulsion is outside the "nanoemulsion" region and has failed to solubilize diclofenac sodium. The solid circles ("●") are acceptable nanoemulsions, open circles ("○") denote compositions that did not form nanoemulsions, and the open squares ("□") are nanoemulsions with high viscosity and limited stability.

In some embodiments, this invention relates to any nanoemulsion composition within the "nanoemulsion region" which is defined by lines between the five critical compositions (A, B, C, D and E), corresponding to a weight % ratio of Phospholipids:Oil:Aqueous Phase of 10:0:86.25 for A, 8:2:86.25 for B, 3:32:61.25 for C, 18:17:61.25 for D and 20:0:76.25 for E.

Nanoemulsions of this invention comprises:
(1) A combined concentration of phospholipids and oil between 10-35% wt. Below 10% wt., the compositions are incapable of solubilizing diclofenac sodium at 3.75%. Above 35% wt., the nanoemulsion can be too viscous to produce and may have compromised stability.
(2) The weight ratio of phospholipids-to-oil generally is
(3) not less than certain values, which depends on the combined concentration of phospholipids and oil as follow:

| Combined concentration of phospholipids and oils (% wt) | Minimal wt. ratio of phospholipids-to-oil |
|---|---|
| About 10 | 4:1 |
| About 15 | 1:1 |
| About 20 | 0.43:1 |
| About 25 | 0.25:1 |

Another ternary phase diagram was drawn (FIG. 2) which depicts a second "nanoemulsion region" (grey area) using the compositions below:

Compositions in FIG. 2

| Composition (% wt.) | Example 32-30 ("H") | Example 32-31 ("I") | Example 32-32 ("J") | Example 32-33 ("K") |
|---|---|---|---|---|
| Diclofenac sodium | 3.75 | 3.75 | 3.75 | 3.75 |
| Medium chain triglyceride | 1 | 7 | 10 | 17 |
| Lecithin | 9 | 8 | 10 | 3 |
| EDTA disodium dehydrate | 0.0055 | 0.0055 | 0.0055 | 0.0055 |
| Sucrose | 5 | 5 | 5 | 5 |
| Purified water | q.s. | q.s. | q.s. | q.s. |

The second "nanoemulsion region" is defined by connecting lines between five critical compositions (F, G, H, and I). Table below exhibits their composition as well as a composition ("L" which is same as the Example 21 composition), which is located in the second "nanoemulsion region".

| Locator ID in the Phase Diagram (FIG. 2) | Phospholipids (% wt) | Oil (% wt) | Aqueous Phase (% wt) |
|---|---|---|---|
| H, solid circle | 9 | 1 | 86.25 |
| I, solid cycle | 8 | 7 | 81.25 |
| J, solid circle | 10 | 10 | 76.25 |
| K, solid circle | 17 | 3 | 76.25 |
| L, same as Example 21 composition, solid circle | 10 | 5 | 81.25 |

Any composition within this second "nanoemulsion region" will not only form an acceptable nanoemulsion but also will be more stable than any composition outside of this region. This "nanoemulsion region" also includes a stable nanoemulsion composition (L: Example 21). The nanoemulsions in the "nanoemulsion region" remain precipitate-free (i.e. no precipitation) when stored for 1 month at 2-8° C. The Example 21 composition remain precipitate-free (i.e. no precipitation) when stored for 12-24 months at 2-8° C.

This invention relates to any nanoemulsion composition within the second "nanoemulsion region" which is defined by lines between the four critical compositions (H, I, J, and K), corresponding to a weight % ratio of Phospholipids:Oil:Aqueous Phase of 9:1:86.25 for H, 8:7:81.25 for 1, 10:10:76.25 for J, and 17:3:76.25 for K.

FIG. 2: Phase diagram depicting a second "nanoemulsion region" region (grey area), which is defined by connecting lines between five critical compositions (H, I, J, and K). Any composition within this region can form a stable nanoemulsion. For example, the Example 21 composition (L) which is one of the compositions in the second "nanoemulsion" region.

A nanoemulsion composition of this invention comprises:
(1) A combined concentration of phospholipids and oil of between about 10 to about 20% wt.
(2) Oil concentration between about 1 to about 10% wt.
(3) Phospholipids concentration between about 8 to about 17% wt., and
(4) A weight ratio of phospholipids-to-oil about 1:1 to 9:1.

Example 33

Fourier transform infrared spectroscopy (FT-IR) and differential scanning calorimetry (DSC) were used to characterize the diclofenac sodium nanoemulsion of Example 21 and can be used to characterize other formulations. A nanoemulsion containing diclofenac sodium ("Example 21") according to Example 21 and a matching nanoemulsion vehicle ("Example 21 Vehicle") having the same composition as Example 21 without diclofenac sodium were prepared as per the procedure mentioned earlier. Both nanoemulsions were dried by removing water under vacuum. A "Physical Mixture" sample was also prepared by mixing dried Example 21 Vehicle with the same amount of diclofenac sodium as in the dried Example 21.

A) FT-IR Analysis

FT-IR spectra were obtained on an ATI/Mattson Genesis FTIR system using the KBr disc method within the scanning range of 4000-370 $cm^{-1}$. The resolution used was 2 $cm^{-1}$ (16 scans/spectrum). Data were analyzed using the software package "Omnic" (version 6.2).

The IR spectra of diclofenac sodium, the dried Example 21 Vehicle, Physical Mixture and the dried Example 21 samples are shown in FIG. 3. The IR spectrum of the dried Example 21 sample is different from all other three with a new peak formed at 1368 $cm^{-1}$. In addition, the peak at 1745.9 $cm^{-1}$ in dried Example 21 sample exhibited a red shift compared to the 1739.2 $cm^{-1}$ in the Physical Mixture. These evidences indicate formation of certain unique intermolecular association and structural feature in the nanoemulsion of this invention.

B) DSC Analysis

DSC analysis was performed on DSC 120 (SSC/5200, SII, Seiko instrument).

The samples in the aluminum pan were heated at the speed of 5° C./min from 30° C. to 380° C. under nitrogen gas.

The DSC thermograms of diclofenac sodium and the dried Example 21 are shown in FIG. 4. Three thermal events were observed for diclofenac sodium including what appeared to be a glass transition event at about 75° C. and two endothermic peaks at 281° C. and 289° C., which are likely related to melting of crystalline diclofenac sodium. However, all these thermal events disappeared in the dried Example 21, indicating that the diclofenac sodium is completely dissolved in the nanoemulsion of this invention.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

The invention claimed is:
1. A parenteral composition in the form of oil-in-water nanoemulsion that comprises:
(a) 2% w/w to 5% w/w of diclofenac or a pharmaceutically acceptable salt thereof,
(b) at least one oil component consisting essentially of a medium-chain triglyceride, wherein the at least one oil component is present between about 1% w/w to about 20% w/w,
(c) at least one phospholipid component, wherein the at least one phospholipid component is present between about 1% w/w to about 20% w/w,
(d) about 60% w/w to about 80% w/w of an aqueous phase,
wherein the total concentration of the medium-chain triglyceride and the phospholipid component is in the range from about 15% w/w to about 35% w/w,
wherein the nanoemulsion has percentage of fat greater than 5 microns (PFAT5) of less than 0.05% when stored at a temperature of about 2-8° C. or about 25° C. for about 12 to about 24 months, and wherein the content of the phospholipid component, the oil component and the aqueous phase within the nanoemulsion region in a ternary phase disgram consisting of a phospholipid component, an oil component and an aqueous phase, and the nanoemulsion region is defined by connecting five compositions (A, B, C, D and E) with lines (A-B; B-C; C-D; D-E, and E-A), but not including the lines, in the said ternary phase diagram and the five compositions (A, B, C, D and E), corresponding to weight ratios of the phospholipid component: the oil component: the aqueous phase of 10:0: 86.25 for A, 8:2:86.25 for B, 3:32:61.25 for C, 18:17: 61.25 for D and 20:0:76.25 for E.

2. The composition of claim 1, wherein the medium chain triglyceride is synthetic or derived from a natural source.

3. The composition of claim 1, wherein the phospholipid component comprises a phosphatidyl choline, a lecithin, phosphatidylethanolamine, phosphatidylglycerol, phosphatidic acid, or a mixture thereof.

4. The composition of claim 1, wherein the phospholipid component is a lecithin.

5. The composition of claim 1, wherein the composition has an osmolality of at least 150 mOsm (milliosmoles).

6. The composition of claim 1, wherein the composition has at least one of the following pharmacokinetic parameters:
 a) $AUC_{(0-t)}$ is at least about 900 ng/mL*h,
 b) $AUC_{(0-t)}$ with coefficient of variation (CV %) less than about 30%,
 c) $AUC_{(0-inf)}$ is at least about 900 ng/mL*h, and
 d) $AUC_{(0-inf)}$ with coefficient of variation (CV %) less than about 30%.

7. The parenteral composition of claim 1 comprising: 2% w/w to 5% w/w of diclofenac or a pharmaceutically acceptable salt thereof, about 5% w/w of medium chain triglycerides, about 10% w/w of lecithin, and about 70% w/w to about 80% w/w of the aqueous phase.

8. The parenteral composition of claim 1, wherein the mean oil droplet diameter is less than 200 nm.

9. The parenteral composition of claim 1, wherein the composition displays an additional peak at about 1360 $cm^{-1}$ to about 1370 $cm^{-1}$ when a sample of the composition is placed in a KBr pellet and subjected to FT-IR analysis.

10. The parenteral composition of claim 1, wherein the composition is substantially free of a thermal event when a sample of the composition is placed in a Differential Scanning calorimeter, wherein the sample is heated at the speed of 5° C./min from 30° C. to 380° C. under nitrogen gas.

11. The composition of claim 1, wherein diclofenac sodium is at a concentration between about 5 mg/mL to about 45 mg/mL.

12. The composition of claim 1, wherein diclofenac sodium is at a concentration of about 18.75 mg/mL or 37.5 mg/mL.

13. The composition of claim 1, wherein
 (a) diclofenac or a pharmaceutically acceptable salt thereof is present at about 3.75% w/w;
 (b) the medium-chain triglyceride is present at about 5% w/w; and
 (c) the phospholipid component is egg lecithin present at about 10% w/w.

* * * * *